(12) United States Patent
Tsuyama et al.

(10) Patent No.: US 10,590,264 B2
(45) Date of Patent: Mar. 17, 2020

(54) PHOTOPOLYMERIZATION INITIATOR, POLYMERIZABLE COMPOSITION, INK JET RECORDING METHOD, AND ACYLPHOSPHINE OXIDE COMPOUND

(71) Applicant: FUJIFILM CORPORATION, Minato-ku, Tokyo (JP)

(72) Inventors: Hiroaki Tsuyama, Kanagawa (JP); Kazuhiro Yokoi, Kanagawa (JP); Kenjiro Araki, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 0 days.

(21) Appl. No.: 16/278,714

(22) Filed: Feb. 19, 2019

(65) Prior Publication Data

US 2019/0177508 A1 Jun. 13, 2019

Related U.S. Application Data

(63) Continuation of application No. PCT/JP2017/026560, filed on Jul. 21, 2017.

(30) Foreign Application Priority Data

Sep. 7, 2016 (JP) .................... 2016-174987

(51) Int. Cl.

| | |
|---|---|
| C08F 2/46 | (2006.01) |
| C08F 2/50 | (2006.01) |
| C08G 61/04 | (2006.01) |
| C08K 5/5397 | (2006.01) |
| C09D 11/38 | (2014.01) |
| C07F 9/53 | (2006.01) |
| C08K 5/5317 | (2006.01) |
| C09D 11/101 | (2014.01) |
| C08K 5/5353 | (2006.01) |

(52) U.S. Cl.
CPC .......... *C08K 5/5397* (2013.01); *C07F 9/5337* (2013.01); *C08F 2/50* (2013.01); *C08K 5/5317* (2013.01); *C08K 5/5353* (2013.01); *C09D 11/101* (2013.01); *C09D 11/38* (2013.01)

(58) Field of Classification Search
CPC ...... C08K 5/5397; C08K 5/5353; C08K 2/50; B41J 2/01; B41M 5/00; C09D 11/38; C07F 9/53
USPC ................. 522/64, 6, 189, 184, 1, 71; 520/1
See application file for complete search history.

(56) References Cited

U.S. PATENT DOCUMENTS

| | | |
|---|---|---|
| 4,447,520 A | 5/1984 | Henne et al. |
| 5,399,770 A | 3/1995 | Leppard et al. |
| 5,767,169 A | 6/1998 | Leppard et al. |
| 6,075,065 A | 6/2000 | Yamazaki et al. |
| 2011/0124763 A1 | 5/2011 | Hinamoto et al. |
| 2015/0344711 A1* | 12/2015 | Shimono .............. C09D 11/101 428/207 |

FOREIGN PATENT DOCUMENTS

| | | |
|---|---|---|
| CN | 103172770 A | 6/2013 |
| JP | S58-77890 A | 5/1983 |
| JP | H05-331217 A | 12/1993 |
| JP | H05-345790 A | 12/1993 |
| JP | H08-81481 A | 3/1996 |

(Continued)

OTHER PUBLICATIONS

International Search Report issued in International Application No. PCT/JP2017/026560 dated Aug. 29, 2017.
Written Opinion of the ISA issued in International Application No. PCT/JP2017/026560 dated Aug. 29, 2017.

(Continued)

*Primary Examiner* — Jessica Whiteley
(74) *Attorney, Agent, or Firm* — SOLARIS Intellectual Property Group, PLLC

(57) ABSTRACT

An acylphosphine oxide compound represented by Formula 1-1 or Formula 2-1 which can be used as a photopolymerization initiator. In Formula 1-1 and Formula 2-1, A represents an m-valent group, L's each independently represent a single bond or a divalent linking group, $R^1$'s each independently represent an alkyl group having 1 to 8 carbon atoms, an aryl group having 6 to 20 carbon atoms, or an alkoxy group having 1 to 4 carbon atoms, $R^2$ and $R^3$ each independently represent an alkyl group, an aryl group, or an alkoxy group, m represents an integer of 3 or more, n1's each independently represent an integer of 0 to 4, and n2's each independently represent an integer of 0 to 5.

15 Claims, No Drawings

(56) References Cited

FOREIGN PATENT DOCUMENTS

| | | |
|---|---|---|
| JP | H10-231340 A | 9/1998 |
| JP | H11-92537 A | 4/1999 |
| JP | H11-322818 A | 11/1999 |
| JP | 2007-39453 A | 2/2007 |
| JP | 2014-185319 A | 10/2014 |
| WO | 2010/008077 A1 | 1/2010 |
| WO | 2013/091521 A1 | 6/2013 |
| WO | WO-2014129213 A1 * | 8/2014 ........... C09D 11/101 |

OTHER PUBLICATIONS

Extended European Search Report dated Aug. 20, 2019, issued in corresponding EP Patent Application No. 17848429.1.
English language translation of the following: Office action dated Nov. 12, 2019 from the JPO in a Japanese patent application No. 2018-538266 corresponding to the instant patent application.

* cited by examiner

PHOTOPOLYMERIZATION INITIATOR, POLYMERIZABLE COMPOSITION, INK JET RECORDING METHOD, AND ACYLPHOSPHINE OXIDE COMPOUND

CROSS-REFERENCE TO RELATED APPLICATIONS

This application is a Continuation of International Application No. PCT/JP2017/026560 filed on Jul. 21, 2017, which claims priority to Japanese Patent Application No. 2016-174987 filed on Sep. 7, 2016. The entire contents of these applications are incorporated herein by reference.

BACKGROUND OF THE INVENTION

1. Field of the Invention

The present disclosure relates to a photopolymerization initiator, a polymerizable composition, an ink jet recording method, and an acylphosphine oxide compound.

2. Description of the Related Art

As polymerizable compositions, generally, polymerizable compounds and polymerization initiators are used. As polymerization initiators, in particular, photopolymerization initiators that generate polymerization initiating species by irradiation with active radiation such as ultraviolet rays, acylphosphine oxide compounds are known.

Examples of acylphosphine oxide compounds of the related art include the compounds described in WO2013/091521A, JP2014-185319A, and JP2007-039453A.

SUMMARY OF THE INVENTION

An object that an embodiment of the present invention intends to achieve is to provide a photopolymerization initiator which is eluted (migrated) from a cured substance to be obtained in a small amount and is excellent in terms of the curing sensitivity and the ink jet jettability in a polymerizable composition, and, additionally, an object that another embodiment of the present invention intends to achieve is to provide a polymerizable composition containing the photopolymerization initiator and an ink jet recording method in which the photopolymerization initiator is used.

In addition, an object that still another embodiment of the present invention intends to achieve is to provide a new acylphosphine oxide compound.

Means for achieving the above-described objects include the following aspects.

<1> A photopolymerization initiator which is an acylphosphine oxide compound represented by Formula 1-1 or Formula 2-1.

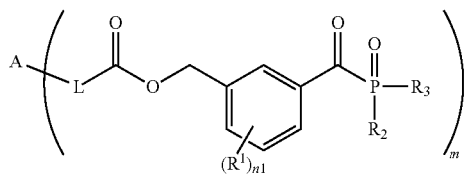

Formula 1-1

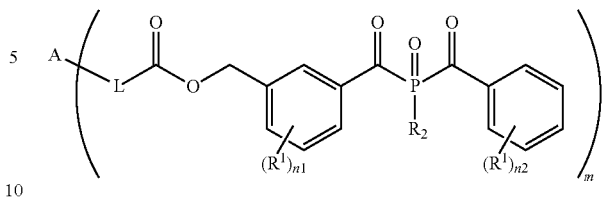

Formula 2-1

In Formula 1-1 and Formula 2-1, A represents an m-valent group, L's each independently represent a single bond or a divalent linking group, $R^1$'s each independently represent an alkyl group having 1 to 8 carbon atoms, an aryl group having 6 to 20 carbon atoms, or an alkoxy group having 1 to 4 carbon atoms, $R^2$ and $R^3$ each independently represent an alkyl group, an aryl group, or an alkoxy group, m represents an integer of 3 or more, n1's each independently represent an integer of 0 to 4, and n2's each independently represent an integer of 0 to 5.

<2> The photopolymerization initiator according to <1>, in which A is an m-valent group obtained by bonding two or more structures selected from the group consisting of a carbon atom, an m-valent hydrocarbon group having 1 to 30 carbon atoms, a mono- or higher-valent hydrocarbon group having 1 to 30 carbon atoms, an oxygen atom, a nitrogen atom, and a sulfur atom.

<3> The photopolymerization initiator according to <1> or <2>, in which A is an m-valent group having a ring structure, an m-valent hydrocarbon group having 1 to 3 carbon atoms, or a carbon atom.

<4> The photopolymerization initiator according to any one of <1> to <3>, in which A is an m-valent group not having any of an amino bond, a thioether bond, and a halogen atom, and L is a divalent linking group not having any of an amino bond, a thioether bond, and a halogen atom or a single bond.

<5> The photopolymerization initiator according to any one of <1> to <4> which is an acylphosphine oxide compound represented by Formula 1-2 or Formula 2-2.

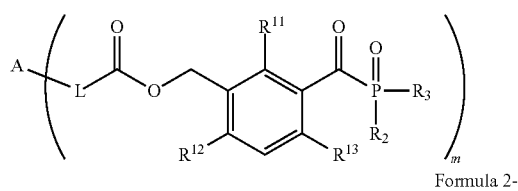

Formula 1-2

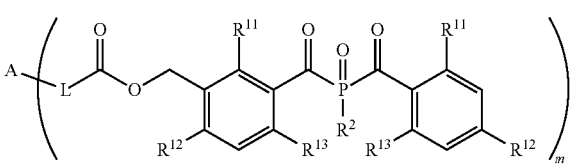

Formula 2-2

In Formula 1-2 and Formula 2-2, A represents an m-valent group, L's each independently represent a single bond or a divalent linking group, $R^2$ and $R^3$ each independently represent an alkyl group, an aryl group, or an alkoxy group, $R^{11}$ to $R^{13}$ each independently represent an alkyl group having 1 to 8 carbon atoms, an aryl group having 6 to 20 carbon atoms, or an alkoxy group having 1 to 4 carbon atoms, and m represents an integer of 3 or more.

<6> The photopolymerization initiator according to any one of <1> to <5>, in which m is an integer of 3 to 5.

<7> The photopolymerization initiator according to any one of <1> to <6>, in which the acylphosphine oxide compound is a compound having a $C_n$ symmetry. Here, n represents an integer of 3 to 24.

<8> A polymerizable composition comprising: the photopolymerization initiator according to any one of <1> to <7>; and a polymerizable compound.

<9> An ink jet recording method comprising: a step of jetting the polymerizable composition according to <8> onto a recording medium using an ink jet method; and a step of curing the polymerizable composition by irradiating the jetted polymerizable composition with active radiation.

<10> An acylphosphine oxide compound represented by Formula 1-1 or Formula 2-1.

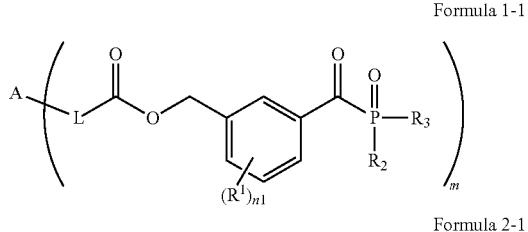

Formula 1-1

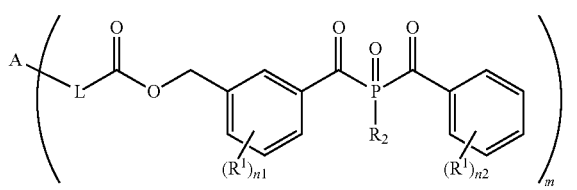

Formula 2-1

In Formula 1-1 and Formula 2-1, A represents an m-valent group, L's each independently represent a single bond or a divalent linking group, $R^1$'s each independently represent an alkyl group having 1 to 8 carbon atoms, an aryl group having 6 to 20 carbon atoms, or an alkoxy group having 1 to 4 carbon atoms, $R^2$ and $R^3$ each independently represent an alkyl group, an aryl group, or an alkoxy group, m represents an integer of 3 or more, n1's each independently represent an integer of 0 to 4, and n2's each independently represent an integer of 0 to 5.

<11> The acylphosphine oxide compound according to <10>, in which A is an m-valent group having a ring structure, an m-valent hydrocarbon group having 1 to 3 carbon atoms, or a carbon atom.

<12> The acylphosphine oxide compound according to <10> or <11>, in which A is an m-valent group not having any of an amino bond, a thioether bond, and a halogen atom, and L is a divalent linking group not having any of an amino bond, a thioether bond, and a halogen atom or a single bond.

<13> The acylphosphine oxide compound according to any one of <10> to <12> represented by Formula 1-2 or Formula 2-2.

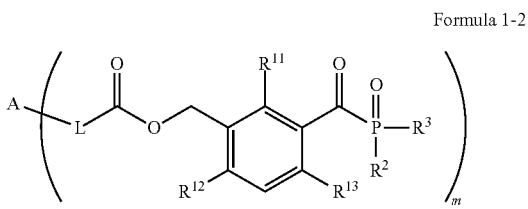

Formula 1-2

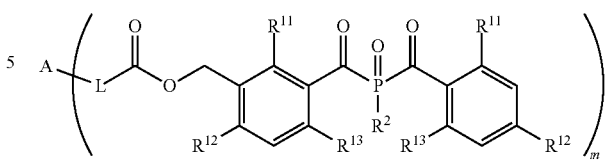

Formula 2-2

In Formula 1-2 and Formula 2-2, A represents an m-valent group, L's each independently represent a single bond or a divalent linking group, $R^2$ and $R^3$ each independently represent an alkyl group, an aryl group, or an alkoxy group, to $R^{13}$ each independently represent an alkyl group having 1 to 8 carbon atoms, an aryl group having 6 to 20 carbon atoms, or an alkoxy group having 1 to 4 carbon atoms, and m represents an integer of 3 or more.

<14> The acylphosphine oxide compound according to any one of <10> to <13>, in which m is an integer of 3 to 5.

<15> The acylphosphine oxide compound according to any one of <10> to <14> having a $C_n$ symmetry, in which n represents an integer of 3 to 24.

According to an embodiment of the present invention, it is possible to provide a photopolymerization initiator which is migrated from a cured substance to be obtained in a small amount and is excellent in terms of the curing sensitivity and the ink jet jettability in a polymerizable composition.

In addition, according to another embodiment of the present invention, it is possible to provide a polymerizable composition containing the photopolymerization initiator and an ink jet recording method in which the photopolymerization initiator is used.

Furthermore, according to still another embodiment of the present invention, it is possible to provide a new acylphosphine oxide compound.

DESCRIPTION OF THE PREFERRED EMBODIMENTS

Hereinafter, the present disclosure will be described in detail.

Meanwhile, in the present specification, an expression of "xx to yy" represents a numerical range including xx and yy.

"(Meth)acrylate" and the like are the same as "acrylate and/or methacrylate" and the like, which is true in the following description.

Unless particularly otherwise described, hydrocarbon groups such as an alkyl group, an aryl group, an alkylene group, and an arylene group in the present disclosure may have a branch or have a ring structure.

In addition, in the present disclosure, "% by mass" is the same as "% by weight", and "parts by mass" is the same as "weight by mass".

In addition, in the present disclosure, a combination of two or more preferred aspects is a more preferred aspect.

In addition, unless particularly otherwise described, the weight-average molecular weight (Mw) in the present disclosure refers to a molecular weight that is detected using a gel permeation chromatography (GPC) analysis device in which columns of TSKgel GMHxL, TSKgel G4000HxL, and TSKgel G2000HxL (all are trade names manufactured by Tosoh Corporation), a solvent of tetrahydrofuran (THF), and a differential refractometer and converted using polystyrene as a standard substance.

Hereinafter, the present disclosure will be described in detail.

(Photopolymerization Initiator)

A photopolymerization initiator according to the embodiment of the present disclosure is an acylphosphine oxide compound represented by Formula 1-1 or Formula 2-1 (hereinafter, also referred to as "specific acylphosphine oxide compound").

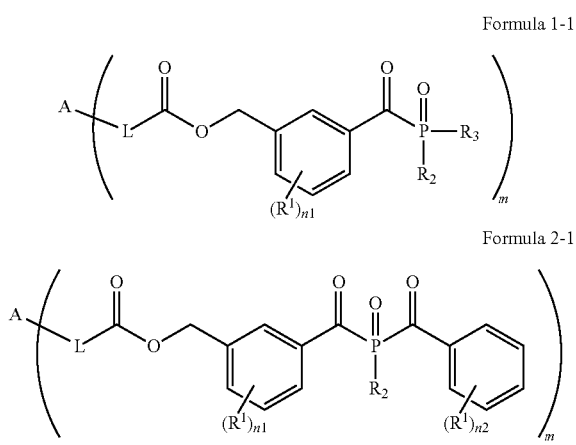

Formula 1-1

Formula 2-1

In Formula 1-1 and Formula 2-1, A represents an m-valent group, L's each independently represent a single bond or a divalent linking group, $R^1$'s each independently represent an alkyl group having 1 to 8 carbon atoms, an aryl group having 6 to 20 carbon atoms, or an alkoxy group having 1 to 4 carbon atoms, $R^2$ and $R^3$ each independently represent an alkyl group, an aryl group, or an alkoxy group, m represents an integer of 3 or more, n1's each independently represent an integer of 0 to 4, and n2's each independently represent an integer of 0 to 5.

The acylphosphine oxide compound is degraded by active radiation and generates a polymerization initiating species such as a radical.

As a result of detailed studies, the present inventors found that, in a case in which the acylphosphine oxide compound represented by Formula 1-1 or Formula 2-1 is used, a photopolymerization initiator which is migrated from a cured substance to be obtained in a small amount and is excellent in terms of the curing sensitivity and the ink jet jettability can be obtained.

The detailed mechanism is not clear; however, in an aromatic ring of an aromatic acyl group that is bonded to a phosphorus atom, in a case in which a location to which a carbonyl group in the acyl group is bonded is substituted into an ortho position or a para position, it is considered that contribution is made to a resonance stabilization effect of a generated radical and the reactivity degrades, and, in the case of having a carbonyloxy methyl structure in a meta position as illustrated in Formula 1-1 or Formula 2-1, it is assumed that the resonance stabilization of the generated radical is suppressed and the curing sensitivity is excellent.

In addition, in the case of having a carbonyloxy methyl structure in the meta position, it is assumed that the mobility of a molecule is limited and the migration amount is suppressed.

Furthermore, in a case in which the molecular weight is large, the ink jet jettability deteriorates due to a high viscosity, and, in a case in which the molecular weight is small, the mobility of a molecule in a film increases, and the migration amount increases. In the case of having a polyvalent (tri- or higher-valent) linking group in the center and having a specific acylphosphine oxide structure at the terminal like the photopolymerization initiator according to the embodiment of the present disclosure, it is assumed that the migration amount is suppressed and the ink jet jettability is also excellent.

In addition, furthermore, in a case in which the photopolymerization initiator according to the embodiment of the present disclosure is added to an ink composition, the preservation stability of the ink composition is excellent. In the case of a photopolymerization initiator of the related art, it is considered that the photopolymerization initiator partially gelatinizes, the component of the photopolymerization initiator is significantly precipitated due to the interaction with other components in the ink composition, and the preservation stability degrades. On the other hand, in a case in which the photopolymerization initiator according to the embodiment of the present disclosure has a carbonyloxy methyl structure, additionally, has a polyvalent (tri- or higher-valent) linking group in the center, and has the specific acylphosphine oxide structure at the terminal, it is assumed that the compatibility with individual components included in the ink composition is excellent and the preservation stability is excellent.

Hereinafter, the present disclosure will be described in detail.

$R^1$'s in Formula 1-1 and Formula 2-1 each are, independently, preferably an alkyl group having 1 to 8 carbon atoms or an alkoxy group having 1 to 4 carbon atoms, more preferably an alkyl group having 1 to 8 carbon atoms, still more preferably an alkyl group having 1 to 4 carbon atoms, and particularly preferably a methyl group. In such an aspect, the curing sensitivity in a polymerizable composition is superior.

In addition, $R^1$'s in Formula 1-1 and Formula 2-1 are all preferably the same group.

$R^2$'s and $R^3$'s in Formula 1-1 and Formula 2-1 each are, independently, preferably an alkyl group having 1 to 8 carbon atoms, an aryl group having 6 to 20 carbon atoms, or an alkoxy group having 1 to 4 carbon atoms, more preferably an aryl group having 6 to 20 carbon atoms or an alkoxy group having 1 to 4 carbon atoms, still more preferably an aryl group having 6 to 20 carbon atoms, particularly preferably an aryl group having 6 to 12 carbon atoms, and most preferably a phenyl group. In such an aspect, the curing sensitivity in a polymerizable composition is superior, and furthermore, the raw materials can be easily procured.

m in Formula 1-1 and Formula 2-1 is preferably an integer of 3 or more and 24 or less, more preferably an integer of 3 or more and 10 or less, still more preferably an integer of 3 or more and 8 or less, particularly preferably an integer of 3 or more and 6 or less, and most preferably an integer of 3 or more and 5 or less. In a case in which m is in the above-described range, the migration amount from a cured substance to be obtained is smaller, the ink jet jettability in a polymerizable composition is superior, and the preservation stability of an ink composition is superior.

n1's in Formula 1-1 and Formula 2-1 each are, independently, preferably an integer of 0 to 3, more preferably 2 or 3, and particularly preferably 3. In such an aspect, the curing sensitivity in a polymerizable composition is superior, and furthermore, the raw materials can be easily procured.

In addition, n1's in Formula 1-1 and Formula 2-1 are all preferably the same number.

n2's in Formula 2-1 each are, independently, preferably an integer of 1 to 3, more preferably 2 or 3, and particularly preferably 3. In such an aspect, the curing sensitivity in a polymerizable composition is superior, and furthermore, the raw materials can be easily procured.

In addition, n2's in Formula 2-1 are all preferably the same number.

From the viewpoint of the migration amount from a cured substance to be obtained and the preservation stability of an ink composition, A in Formula 1-1 and Formula 2-1 is preferably an m-valent group obtained by bonding two or more structures selected from the group consisting of a carbon atom (a tetravalent carbon atom), an m-valent hydrocarbon group having 1 to 60 carbon atoms, a mono- or higher-valent hydrocarbon group having 1 to 60 carbon atoms, an oxygen atom, a nitrogen atom, and a sulfur atom, more preferably an m-valent group obtained by bonding two or more structures selected from the group consisting of a carbon atom, an m-valent hydrocarbon group having 1 to 20 carbon atoms, a mono- or higher-valent hydrocarbon group having 1 to 20 carbon atoms, an oxygen atom, a nitrogen atom, and a sulfur atom, and still more preferably a carbon atom or an m-valent hydrocarbon group having 1 to 20 carbon atoms.

The hydrocarbon group may be an aliphatic hydrocarbon group, an aromatic hydrocarbon group, or a combined group of one or more aliphatic hydrocarbon groups and one or more aromatic hydrocarbon groups. In addition, the aliphatic hydrocarbon group may have an unsaturated bond.

In addition, the hydrocarbon group may further have a substituent. Examples of the substituent include a halogen atom, an alkoxy group, an acyl group, an alkoxycarbonyl group, an amide group, and an acyloxy group.

In addition, from the viewpoint of the migration amount from a cured substance to be obtained, the curing sensitivity, and the ink jet jettability, A in Formula 1-1 and Formula 2-1 is preferably an m-valent group having a ring structure, an m-valent hydrocarbon group having 1 to 3 carbon atoms, or a carbon atom, more preferably an m-valent group having a ring structure, one hydrogen atom on a tetravalent carbon atom, a hydrocarbon group having 1 to 20 carbon atoms, a hydroxyl group, a trivalent hydrocarbon group having a nitro group or an amino group, or a carbon atom, and particularly preferably an m-valent aromatic hydrocarbon group or a carbon atom.

Meanwhile, the m-valent aromatic hydrocarbon group may be a monocyclic aromatic hydrocarbon group, an aromatic hydrocarbon group of a fused ring obtained by fusing two or more rings, or an aromatic hydrocarbon group of two or more rings that are not fused together.

As the A, specifically, the following groups are preferably exemplified. Meanwhile, a wavy line portion represents a bonding position to other structures such as L.

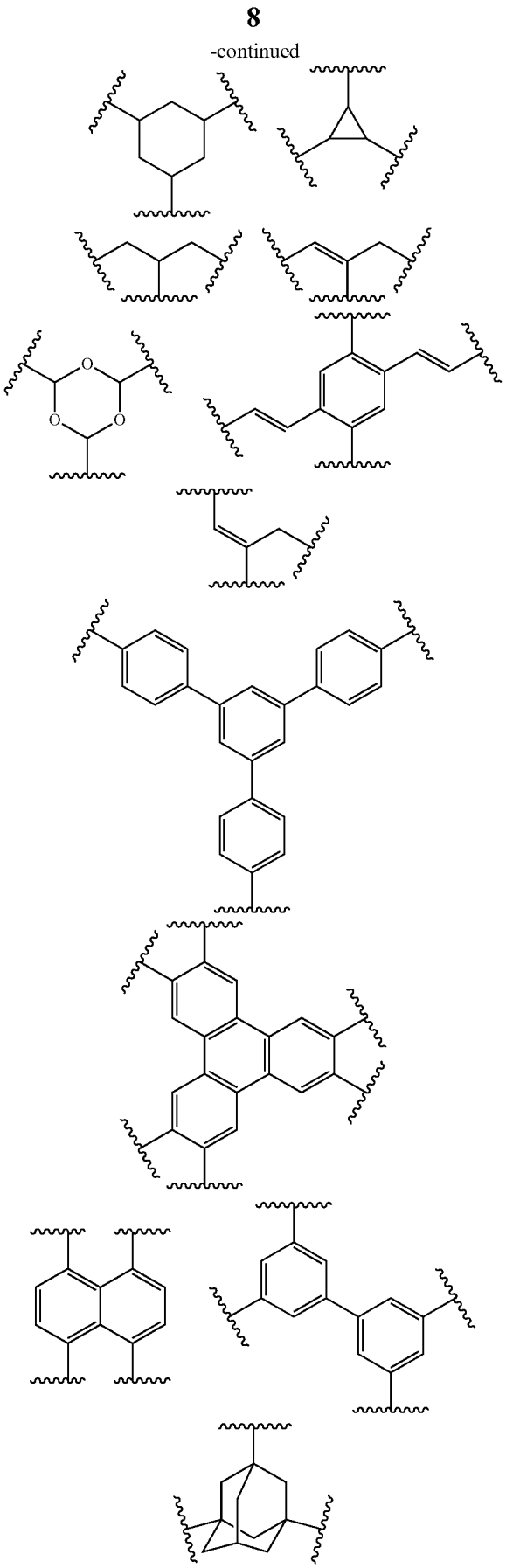

-continued

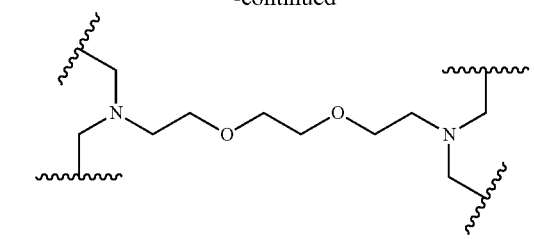
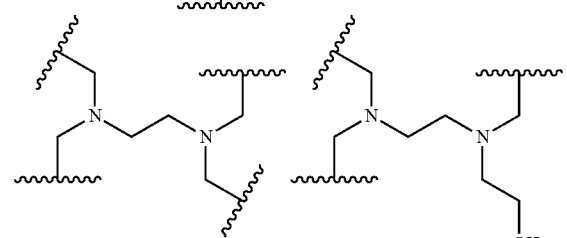
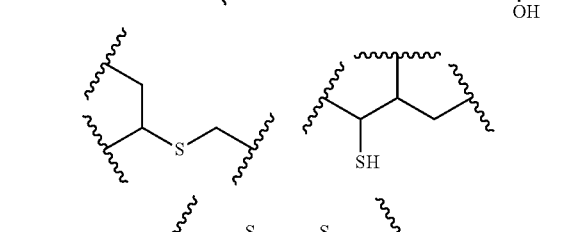
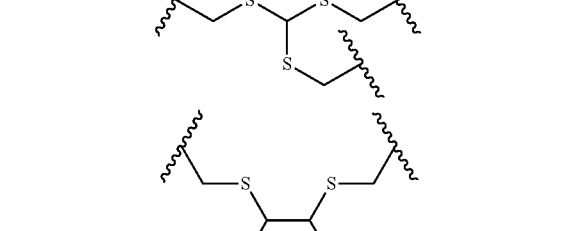
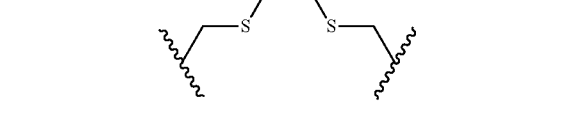

In the above-illustrated structures, $R^A$ represents a hydrogen atom, a hydrocarbon group having 1 to 20 carbon atoms, a hydroxyl group, a nitro group, or an amino group.

From the viewpoint of the migration amount, the curing sensitivity, and the ink jet jettability, L's in Formula 1-1 and Formula 2-1 each are, independently, preferably a single bond, a divalent alkylene group, or a group obtained by combining two or more divalent alkylene groups and ether bonds and more preferably a single bond, a divalent alkylene group having 1 to 8 carbon atoms, or a group having 1 to 20 carbon atoms obtained by combining two or more divalent alkylene groups having 1 to 8 carbon atoms and ether bonds.

In addition, from the viewpoint of the migration amount and the curing sensitivity, L in Formula 1-1 and Formula 2-1 is preferably a group that is bonded to the ester bond in Formula 1-1 and Formula 2-1 through a carbon atom.

Furthermore, m L's in Formula 1-1 and Formula 2-1 are all preferably the same group (including the single bond).

In addition, as a group obtained by combining A and m L's in Formula 1-1 and Formula 2-1, the following groups are preferably exemplified.

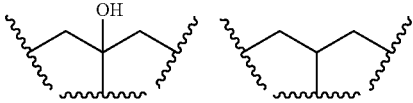
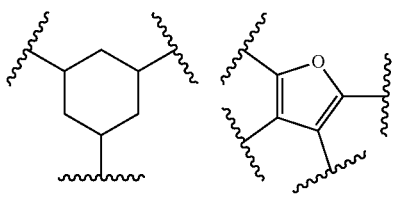
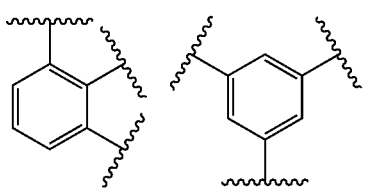
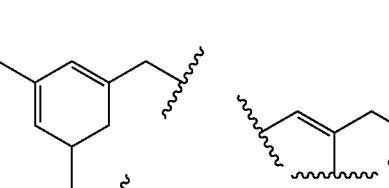
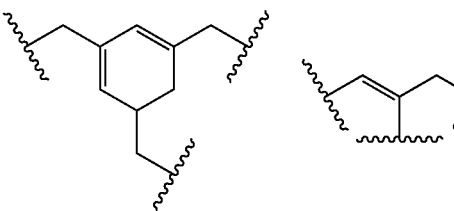
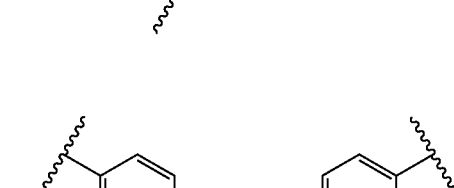
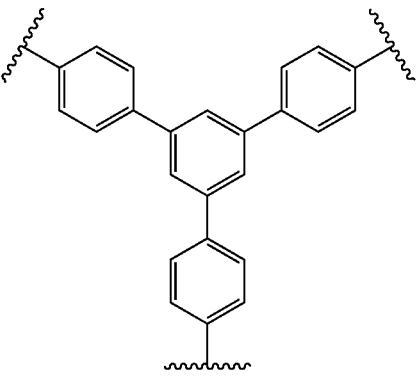
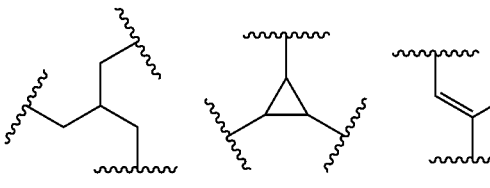

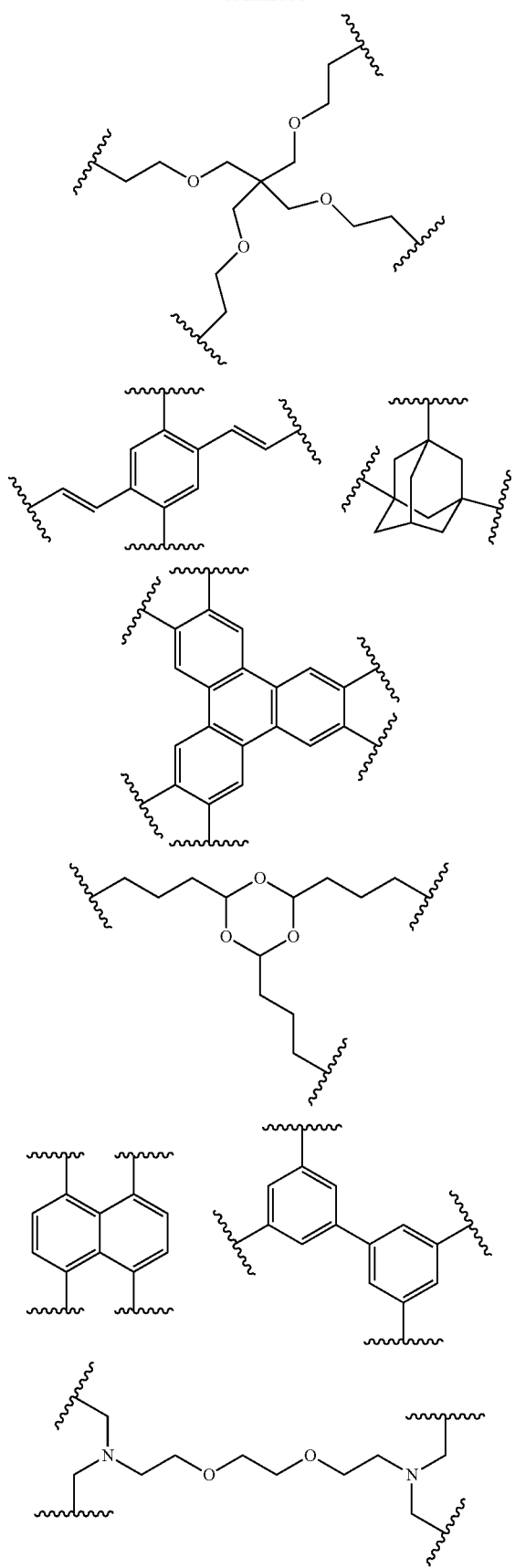
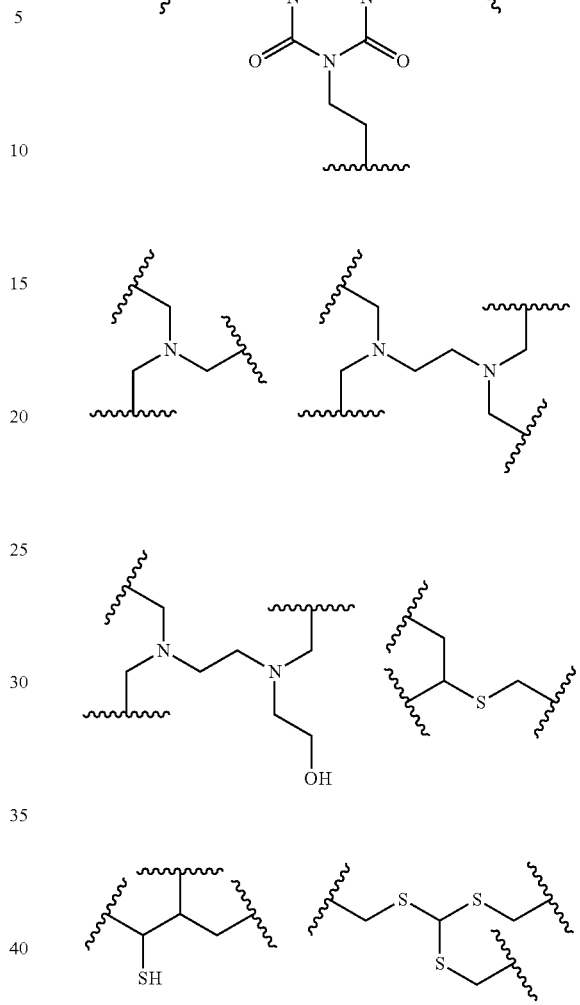

In addition, A in Formula 1-1 and Formula 2-1 is preferably an m-valent group not having any of an amino bond (a divalent or trivalent nitrogen atom), a thioether bond, and a halogen atom, and L in Formula 1-1 and Formula 2-1 is preferably a divalent linking group not having any of an amino bond, a thioether bond, and a halogen atom. In such an aspect, the cutting of chemical bonds in the above-described portions during exposure is suppressed, and the amount of the elution (migration) of a specific acylphosphine oxide compound-derived compound from a cured substance polymerized using the specific acylphosphine oxide compound is suppressed.

The specific acylphosphine oxide compound is preferably a compound having a $C_n$ symmetry. Here, n represents an integer of 3 to 24. In such an aspect, the migration amount from a cured substance to be obtained is smaller, and the curing sensitivity in a polymerizable composition is superior.

Regarding the compound having a $C_n$ symmetry of a compound in the present disclosure, in a certain molecule, in a case in which the shape before an intrinsic rotation $C_n$ operation and the shape after the intrinsic rotation $C_n$ operation are not differentiable from each other regardless of the conformational isomer, the compound is considered to have a $C_n$ symmetric element. The intrinsic rotation refers to a single time of rotation around an axis that passes through the molecule at an angle of $2\pi/n$ or $360°/n$.

In addition, the $C_n$ symmetry of a compound in the present disclosure is not a property that regulates the symmetry of a strict steric structure such as a conformational isomer, and, for example, structures illustrated below are considered to have a $C_3$ symmetry and a $C_4$ symmetry respectively.

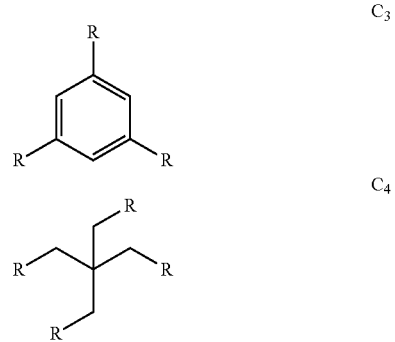

Meanwhile, all of R's represent a group that is the same chemical structure.

n in the $C_n$ symmetry is preferably an integer of 3 or more and 24 or less, more preferably an integer of 3 or more and 12 or less, still more preferably an integer of 3 or more and 6 or less, and particularly preferably 3 or 4. In a case in which n is in the above-described range, the migration amount from a cured substance to be obtained is smaller, the curing sensitivity in a polymerizable composition is superior, and furthermore, the ink jet jettability is superior.

The specific acylphosphine oxide compound is preferably an acylphosphine oxide compound represented by Formula 1-2 or Formula 2-2 from the viewpoint of the migration amount, the curing sensitivity, and the ink jet jettability.

Formula 1-2

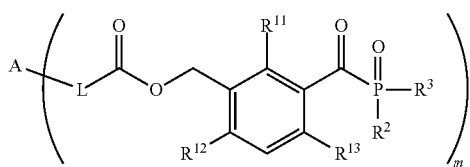

Formula 2-2

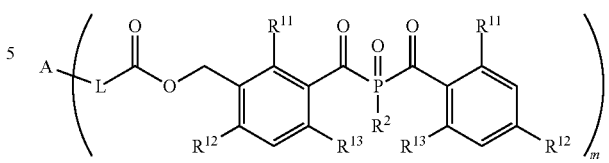

In Formula 1-2 and Formula 2-2, A represents an m-valent group, L's each independently represent a single bond or a divalent linking group, $R^2$ and $R^3$ each independently represent an alkyl group, an aryl group, or an alkoxy group, $R^{11}$ to $R^{13}$ each independently represent an alkyl group having 1 to 8 carbon atoms, an aryl group having 6 to 20 carbon atoms, or an alkoxy group having 1 to 4 carbon atoms, and m represents an integer of 3 or more.

In Formula 1-2 and Formula 2-2, A, L, $R^2$, $R^3$, and m are identical to A, L, $R^2$, $R^3$, and m in Formula 1-1 and Formula 2-1, and preferred aspects thereof are also identical.

$R^{11}$ to $R^{13}$ in Formula 1-2 and Formula 2-2 each are, independently, preferably an alkyl group having 1 to 8 carbon atoms or an alkoxy group having 1 to 4 carbon atoms, more preferably an alkyl group having 1 to 8 carbon atoms, still more preferably an alkyl group having 1 to 4 carbon atoms, and particularly preferably a methyl group. In such an aspect, the curing sensitivity in a polymerizable composition is superior.

In addition, $R^{11}$ to $R^{13}$ in Formula 1-2 and Formula 2-2 are all preferably the same group.

The molecular weight or the weight-average molecular weight (Mw) of the specific acylphosphine oxide compound is preferably 500 or more, more preferably 500 to 10,000, and still more preferably 500 to 5,000 from the viewpoint of the migration amount, the curing sensitivity, and the ink jet jettability.

Meanwhile, in the present disclosure, a compound having a molecular weight distribution is a compound the weight-average molecular weight of which is measured using the above-described method, and a compound having no molecular weight distribution is a compound the molecular weight of which is obtained from the element composition (compositional formula).

In addition, the specific acylphosphine oxide compound is preferably an acylphosphine oxide compound represented by Formula 1-1 from the viewpoint of the migration amount and is preferably an acylphosphine oxide compound represented by Formula 2-1 from the viewpoint of the curing sensitivity, and preferred specific examples of the specific acylphosphine oxide compound will be illustrated below, but are not limited thereto.

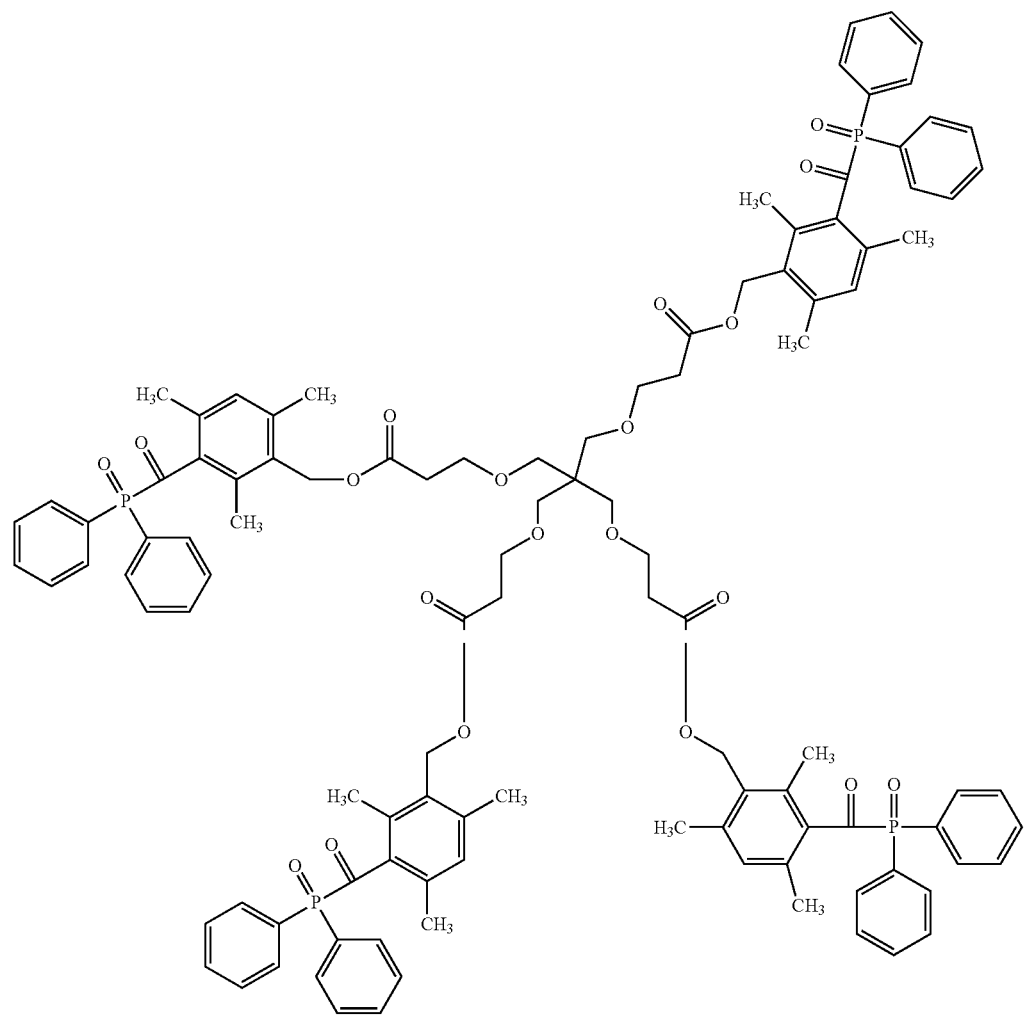
A-1
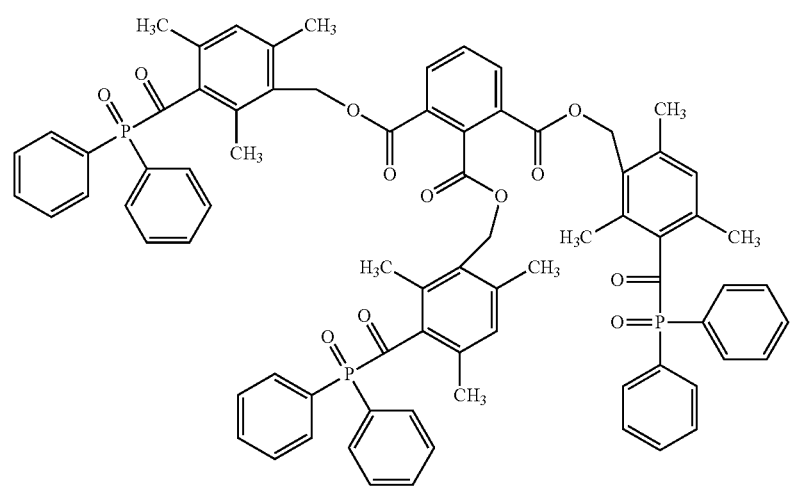
A-2

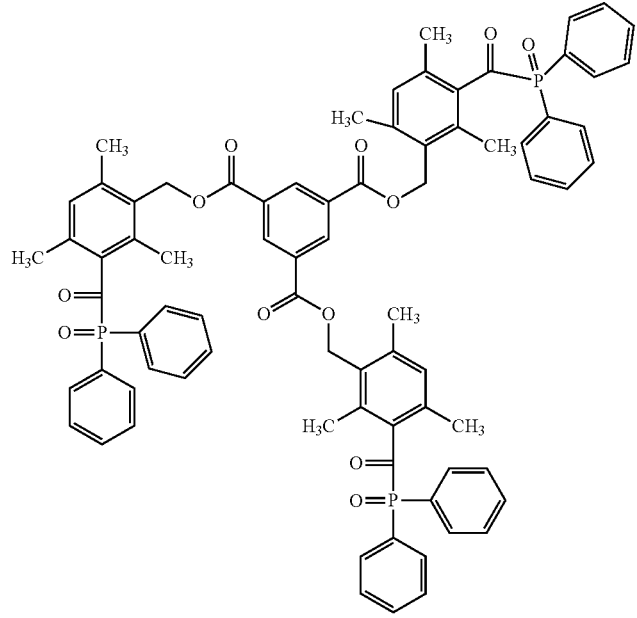
A-3
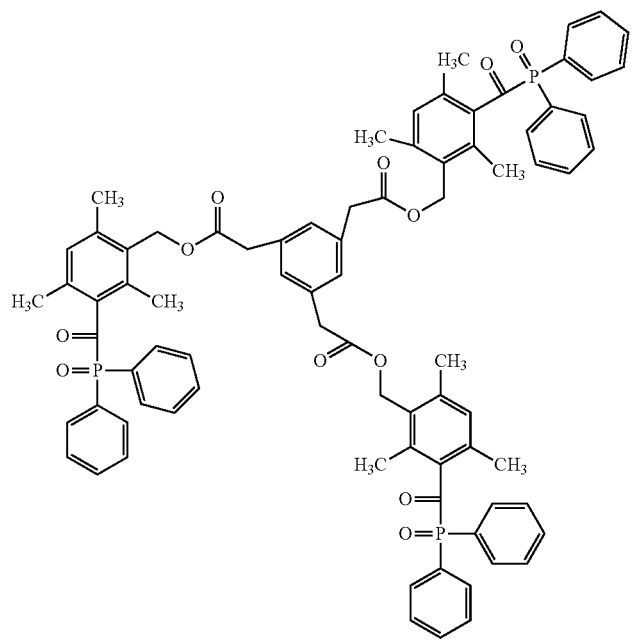
A-4
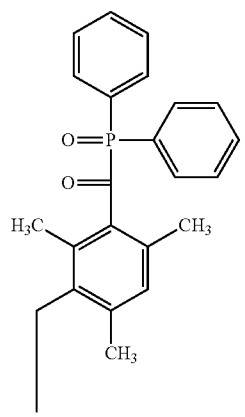
A-5

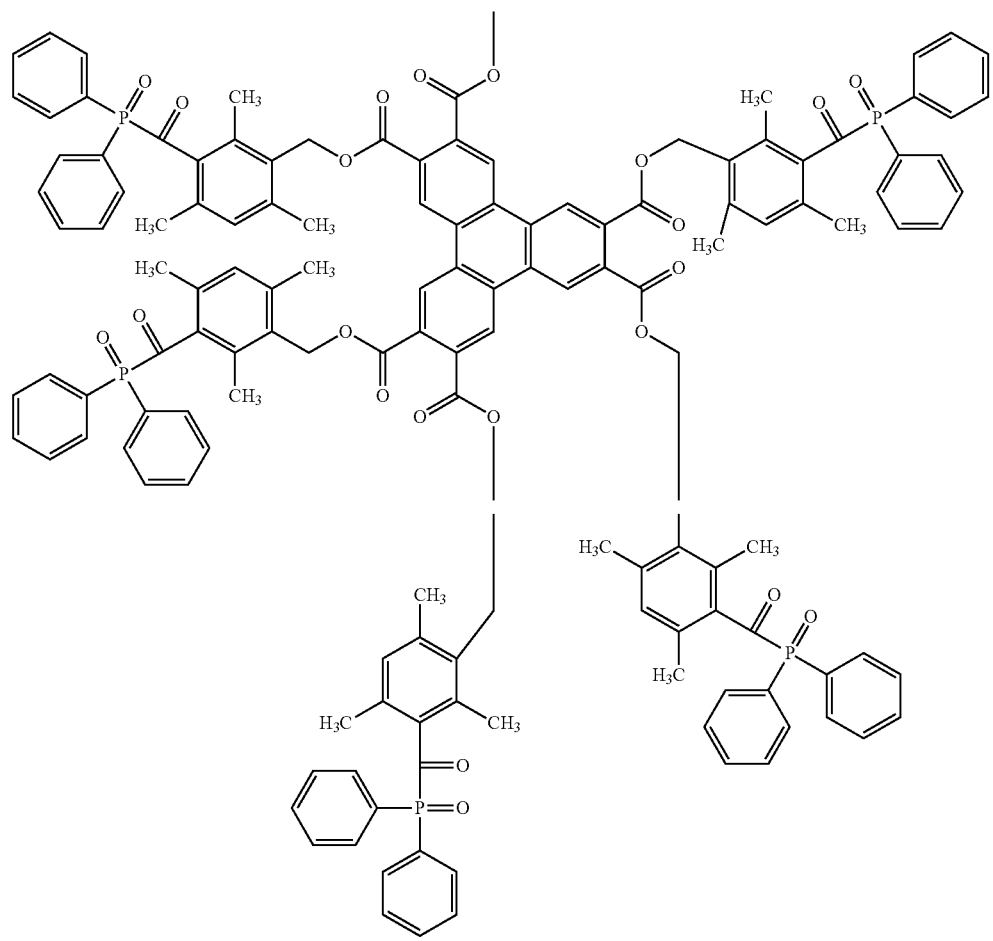
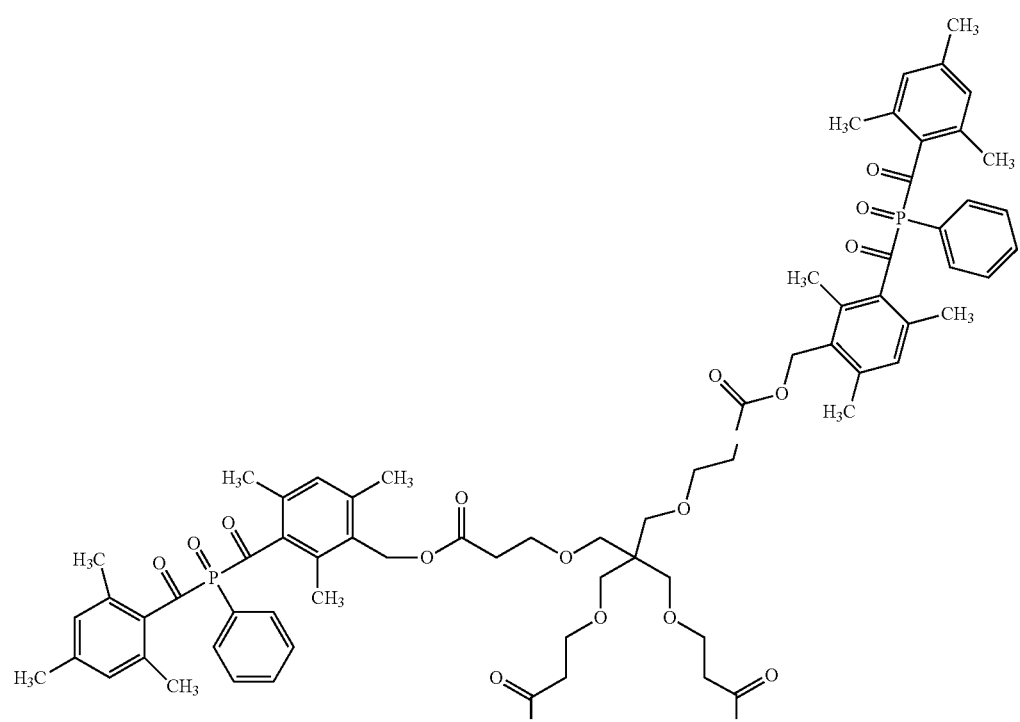
A-6

-continued
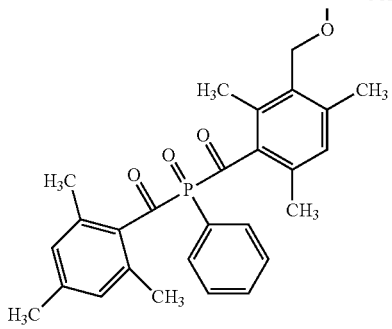
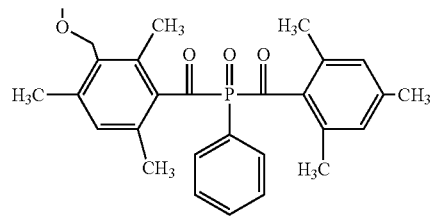
A-7
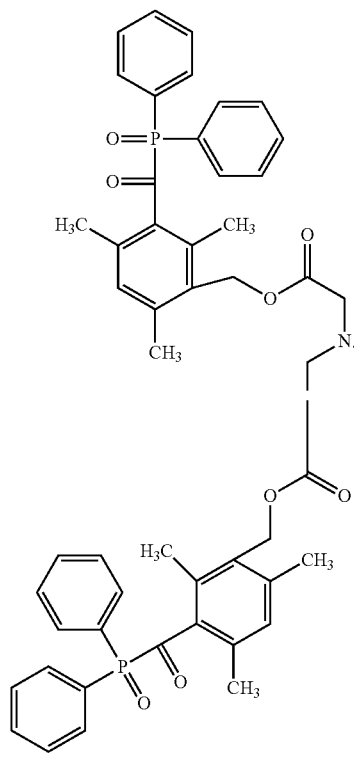
A-8
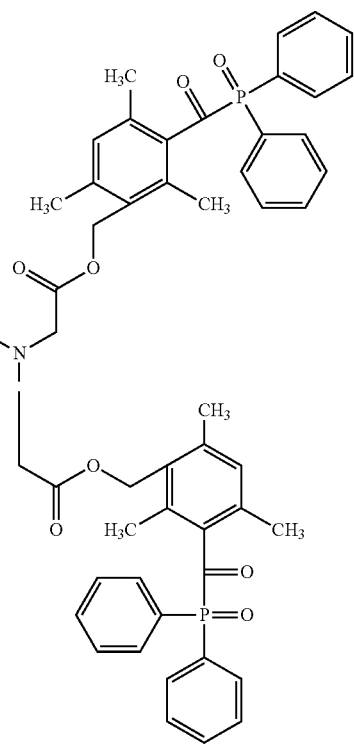
A-9
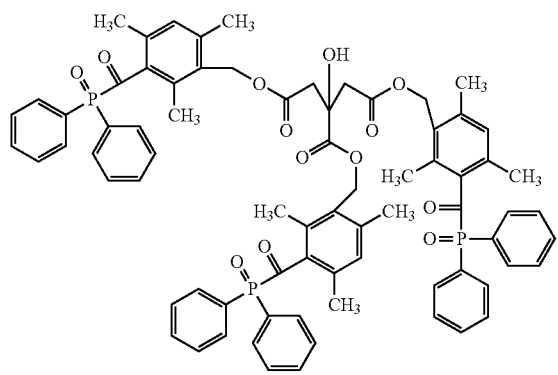
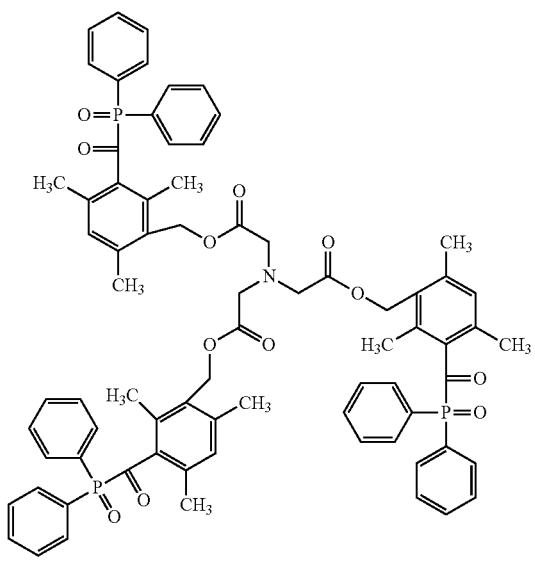

-continued
A-10
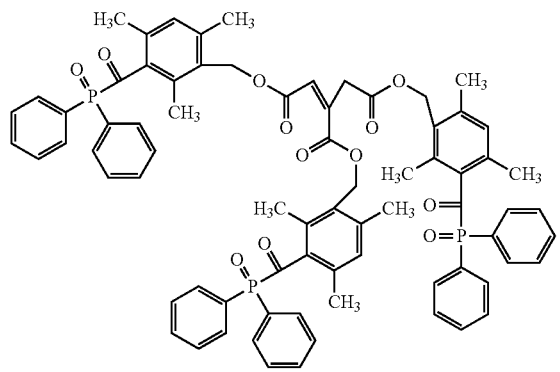
A-11
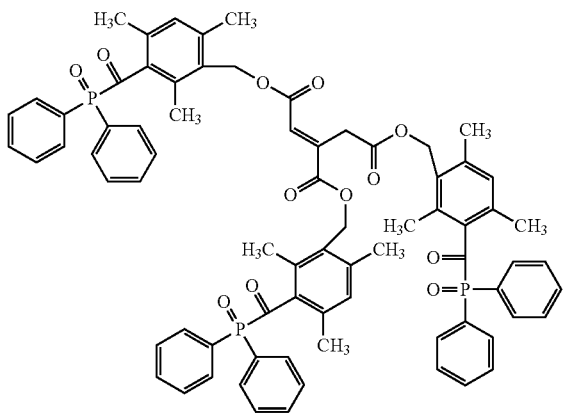
A-12
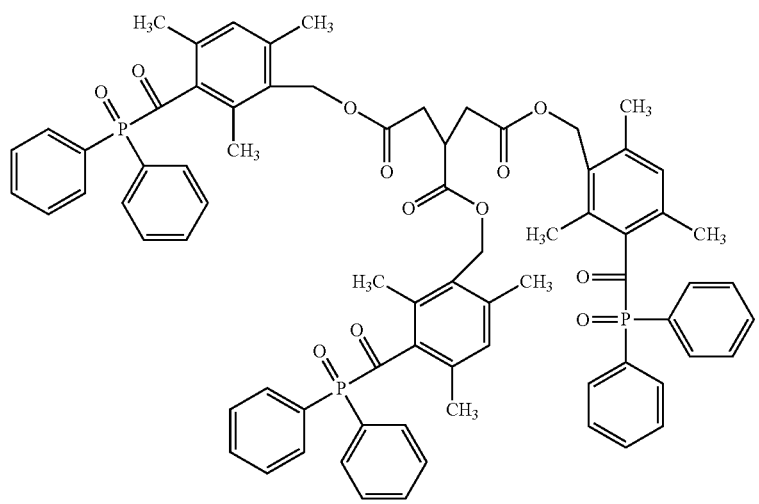
A-13
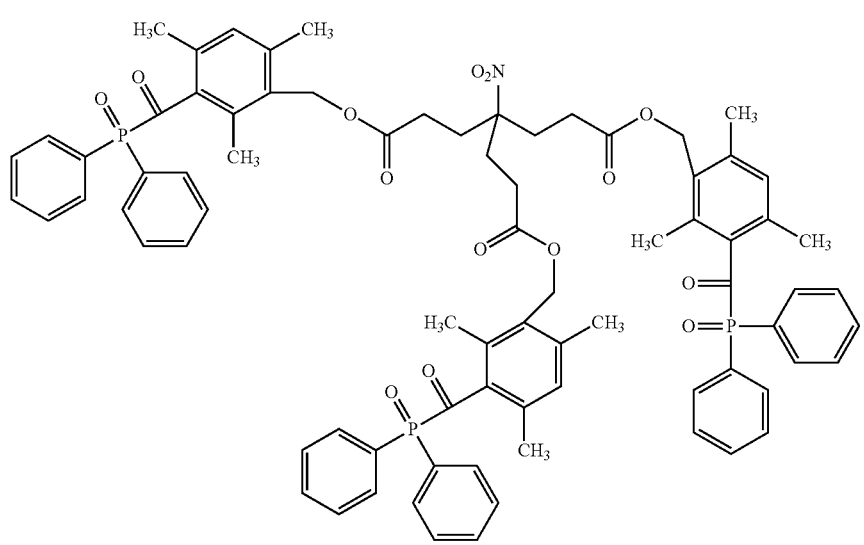

A-14
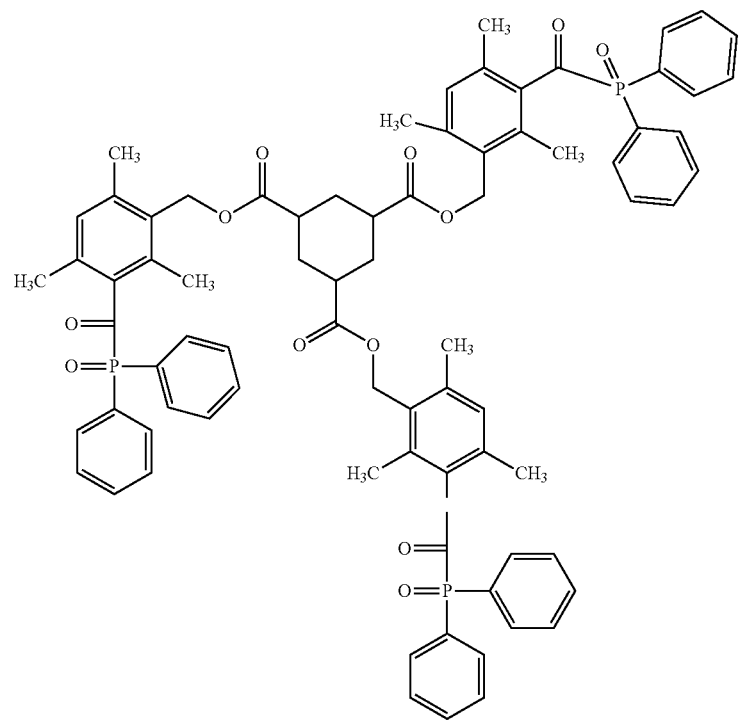
A-15
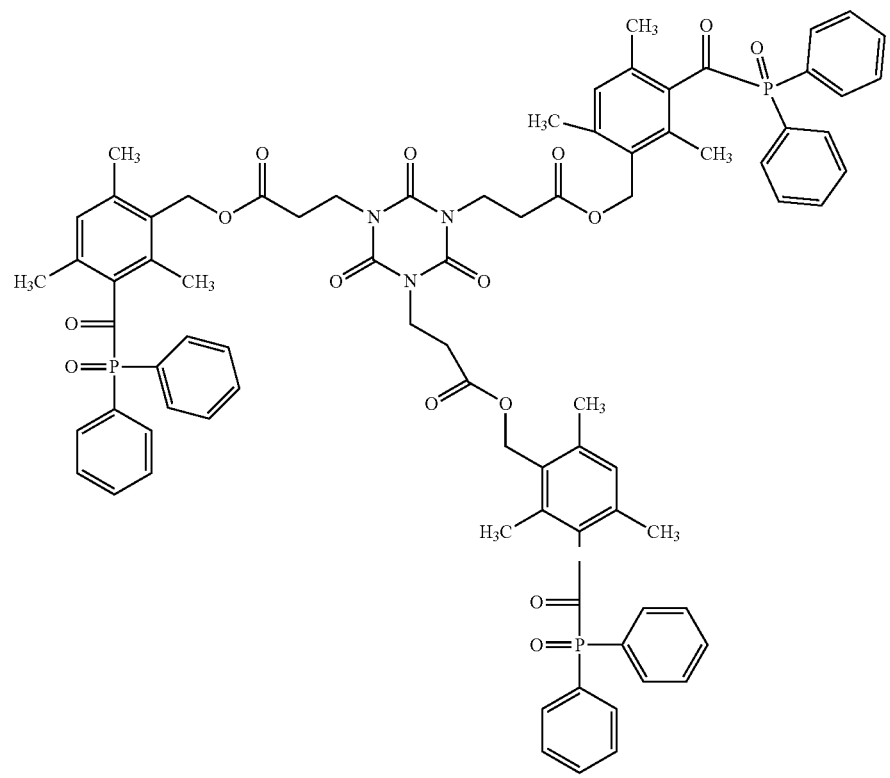

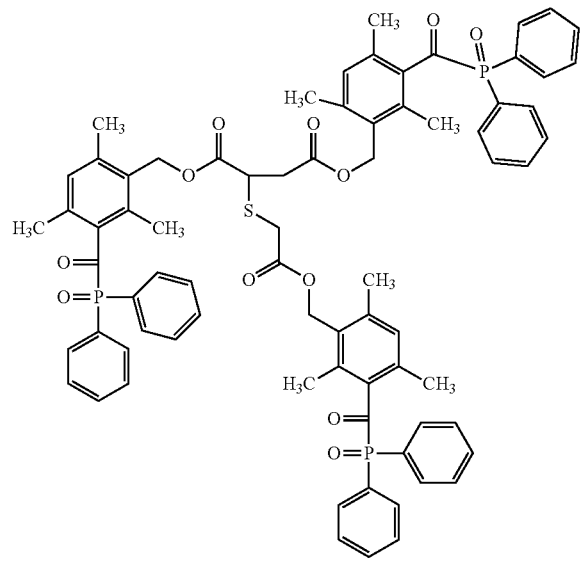
A-16
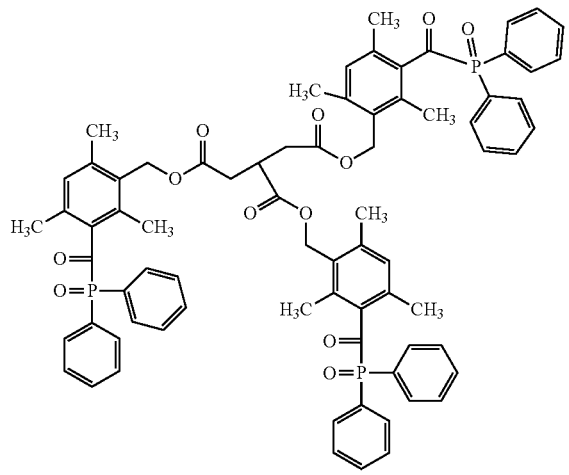
A-17
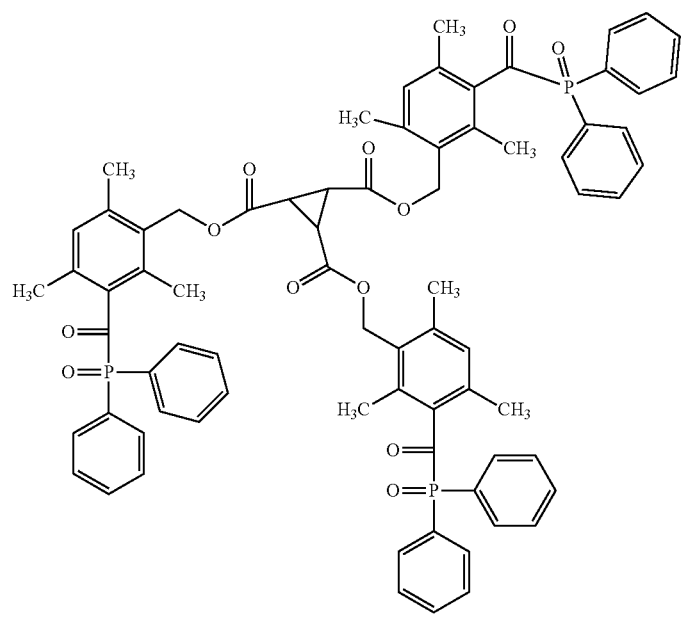
A-18

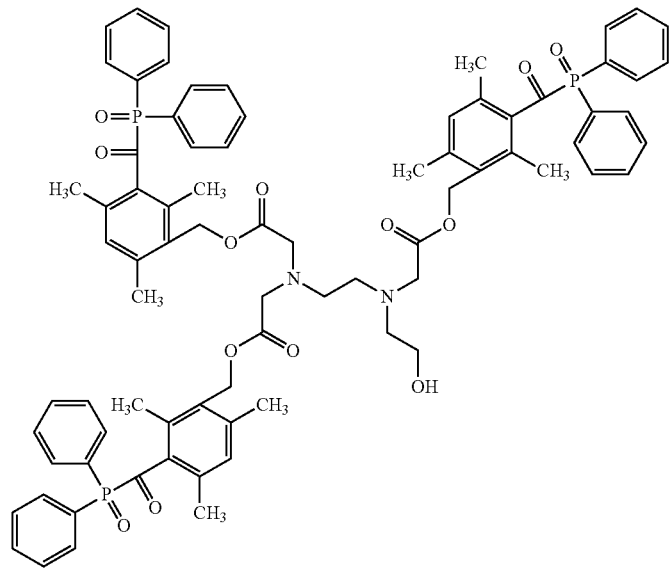
A-19
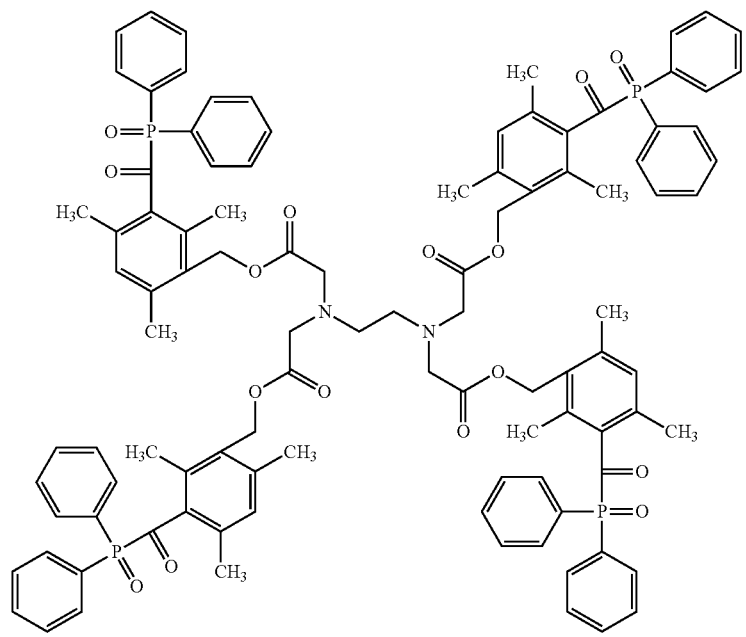
A-20

-continued
A-21
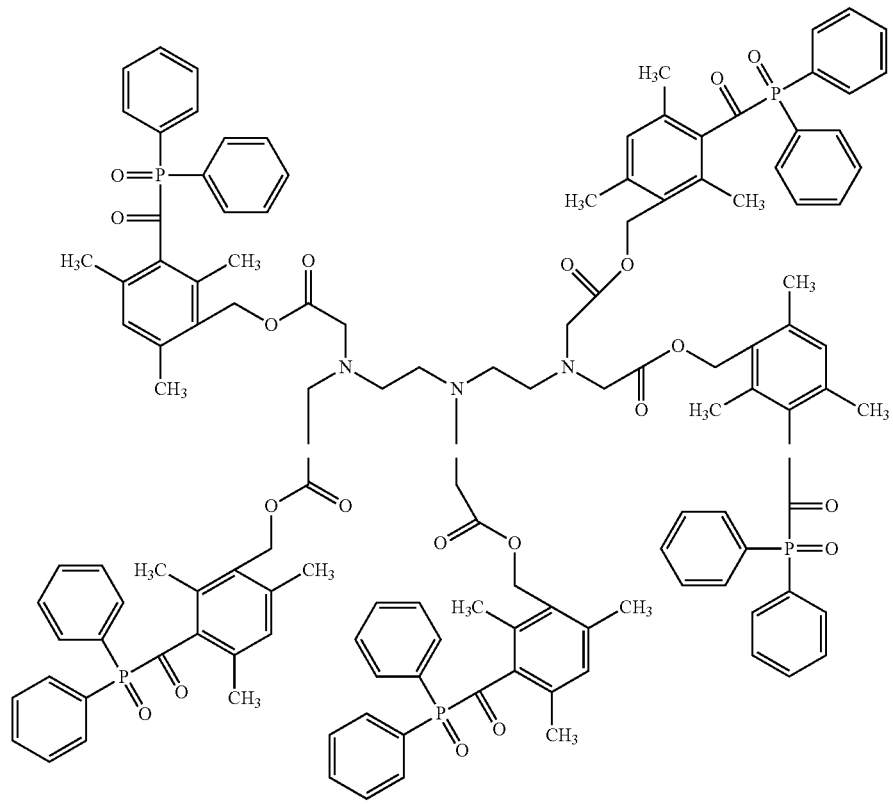
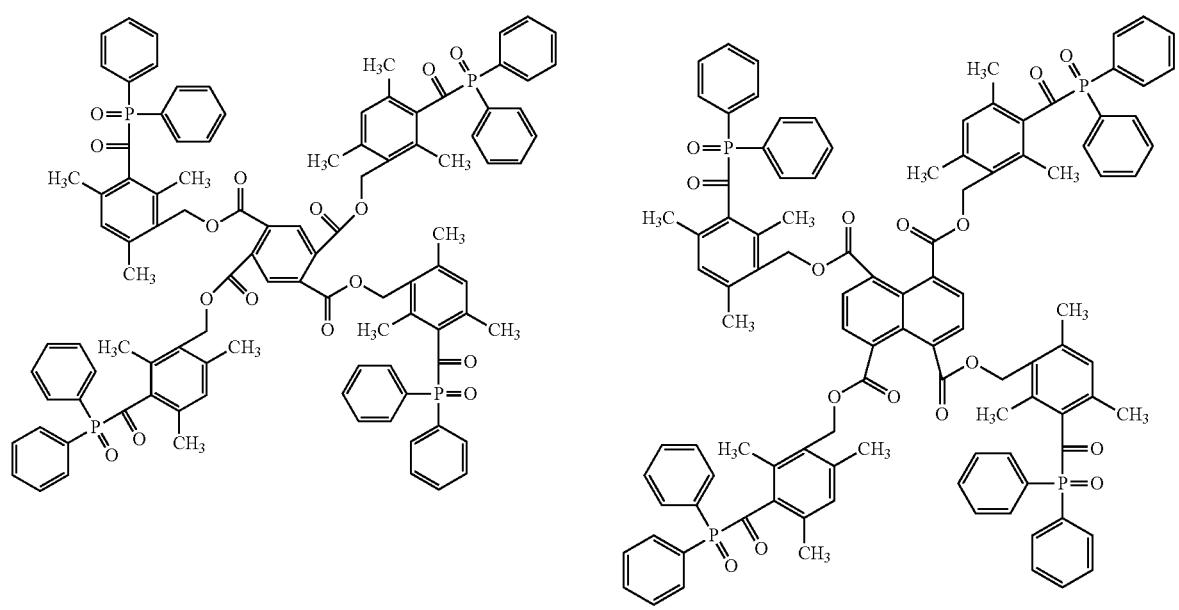
A-22
A-23

-continued
A-24
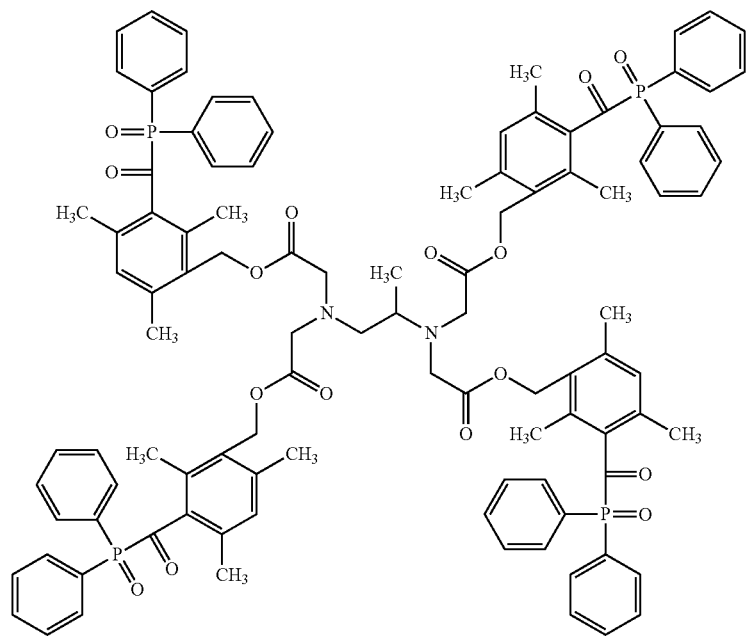
A-25
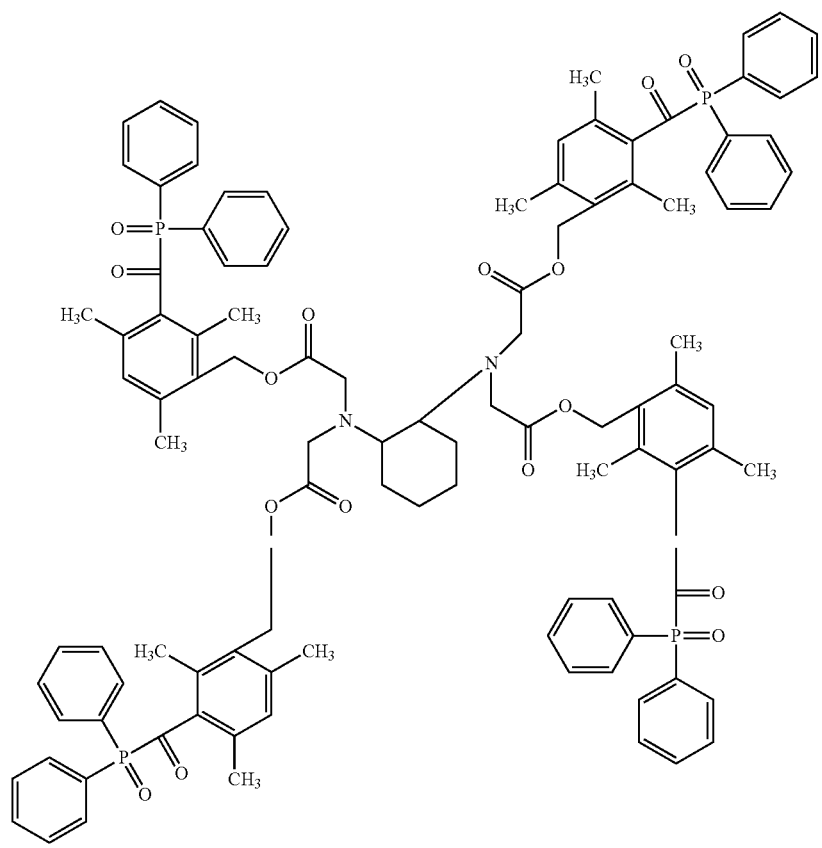

Among these, A-1 to A-6, A-8, A-10 to A-12, A-14, A-17, A-18, A-22, or A-23 is preferred.

<Method for Producing Specific Acylphosphine Oxide Compound>

A method for producing the specific acylphosphine oxide compound is not particularly limited, but a method in which a compound having a methyl halide group on an aromatic ring of an aromatic acyl group of an acylphosphine oxide structure and a polyfunctional carboxylic acid compound are reacted with each other under a basic condition to be esterified is preferably exemplified.

The reaction temperature and the reaction time in the esterification reaction are not particularly limited and may be appropriately set depending on the progress status of the reaction.

In the esterification reaction, a solvent is preferably used. The solvent is not particularly limited, and a polar organic solvent is preferably exemplified.

In addition, after the esterification reaction, purification is preferably carried out using a well-known method such as column, thin layer chromatography (TLC), recrystallization, or reprecipitation.

As a method for producing the compound having a methyl halide group on an aromatic ring of an aromatic acyl group of an acylphosphine oxide structure, the compound can be easily and efficiently produced by causing a Friedel-Crafts reaction of an acylphosphine oxide compound in the presence of a Lewis acid using a methyl halide ether compound.

The Lewis acid being used is preferably a zinc compound such as zinc chloride, zinc bromide, or zinc acetate, an aluminum compound such as aluminum chloride, aluminum bromide, or diethylaluminum chloride, an iron compound such as iron chloride or iron bromide, a bismuth compound such as bismuth (III) chloride, a boron compound such as boron trifluoride, boron trichloride, or tris(pentafluorophenyl) boron, a titanium compound such as titanium tetrachloride, a zirconium compound such as zirconium chloride, a tin compound such as tin tetrachloride or tin trichloride, an indium compound such as indium chloride, or a trifluoromethane sulfonic acid compound that is stable in water or a hydrate thereof such as copper (II) trifluoromethanesulfonate, lanthanum (III) trifluoromethanesulfonate, zinc (II) trifluoromethanesulfonate, silver trifluoromethanesulfonate, ytterbium (III) trifluoromethanesulfonate, scandium (III) trifluoromethanesulfonate, hafnium (IV) trifluoromethanesulfonate, or ytterium (III) trifluoromethanesulfonate, more preferably an aluminum compound, an iron compound, a tin compound, or a zinc compound, and particularly preferably an aluminum compound, an iron compound, or a zinc compound. In the case of the above-described aspect, reactivity and compound stability are excellent, and furthermore, raw materials can be easily procured.

The reaction temperature and the reaction time in the Friedel-Crafts reaction are not particularly limited, may be appropriately set depending on the progress status of the reaction. In the Friedel-Crafts reaction, a solvent is preferably used. The solvent is not particularly limited, and examples thereof include a halogen-based solvent, an aliphatic hydrocarbon-based solvent, and nitrobenzene. Among these, a halogen-based solvent is preferred, and dichloromethane is particularly preferred.

In addition, after the Friedel-Crafts reaction, purification is preferably carried out using a well-known method such as column, thin layer chromatography (TLC), recrystallization, or reprecipitation.

(Polymerizable Composition)

A polymerizable composition according to the embodiment of the present disclosure includes the photopolymerization initiator according to the embodiment of the present disclosure and a polymerizable compound.

The polymerizable composition according to the embodiment of the present disclosure is an ink composition that can be cured by active radiation. The "active radiation" refers to radiation capable of imparting energy that generates initiating species in the polymerizable composition by irradiation with the active radiation, and examples thereof include an $\alpha$ ray, a $\gamma$ ray, an X-ray, an ultraviolet ray, a visible light ray, an electron beam, and the like. Among these, from the viewpoint of curing sensitivity and the ease of device procurement, an ultraviolet ray and electron beam are preferred, and an ultraviolet ray is more preferred.

In addition, the polymerizable composition according to the embodiment of the present disclosure is an active radiation-curable polymerizable composition and is preferably an oily polymerizable composition. The polymerizable composition according to the embodiment of the present disclosure preferably does not contain water and a volatile solvent as much as possible, and, even in a case in which the polymerizable composition contains water and a volatile solvent, the content thereof is preferably 5% by mass or less, more preferably 1% by mass or less, and still more preferably 0.5% by mass or less of the total mass of the polymerizable composition.

In addition, the polymerizable composition according to the embodiment of the present disclosure can be used in a variety of uses such as an ink composition, a resist, an image recording layer of a planographic printing plate, a coating agent, paint, an adhesive, a pressure sensitive adhesive, a coating, a functional film, a film, an optical material, a printing plate material, a semiconductor material, a recording material, a paper additive, a medical material, plastic, a functional gel, and a cosmetic material. Among these, the polymerizable composition preferably can be used as an ink composition and more preferably can be used as an ink composition for ink jet recording (also referred to as "ink jet ink composition").

In the polymerizable composition according to the embodiment of the present disclosure, one kind of the photopolymerization initiator according to the embodiment of the present disclosure may be used singly or two or more kinds of the photopolymerization initiators may be jointly used.

The content of the photopolymerization initiator according to the embodiment of the present disclosure in the polymerizable composition according to the embodiment of the present disclosure is not particularly limited, but is preferably 0.1% to 20% by mass, more preferably 1% to 15% by mass, still more preferably 3% to 10% by mass, and particularly preferably 4% to 8% by mass of the total mass of the polymerizable composition. In the above-described range, the curing property is excellent.

<Polymerizable Compound>

The polymerizable composition according to the embodiment of the present disclosure includes a polymerizable compound.

The polymerizable compound is not particularly limited as long as the polymerizable compound is a compound which causes a polymerization reaction by imparting any type of energy to be cured and can be used in any form of a monomer, an oligomer, or a polymer, but a variety of well-known polymerizable monomers that are known as radical polymerizable monomers causing a polymerization reaction from an initiating species that is generated from a polymerization initiator which is added as desired are particularly preferred.

In addition, the polymerizable compound is preferably an ethylenically unsaturated compound.

One kind of the polymerizable compound can be used singly or two or more kinds of the polymerizable compounds can be used in a mixed form for the purpose of adjusting the reaction rate, the physical properties of cured films, the physical property of the composition, and the like. In addition, the polymerizable compound may be a monofunctional compound or a polyfunctional compound. There is a tendency that an increase in the fraction of the monofunctional polymerizable compound is more likely to produce a soft cured substance and an increase in the fraction of the polyfunctional polymerizable compound produces a superior curing property. Therefore, the fractions of the monofunctional polymerizable compound and the polyfunctional polymerizable compound are randomly determined depending on use.

As the polymerizable compound, it is possible to preferably use a variety of well-known radical polymerizable compounds that cause a polymerization reaction from an initiating species which is generated from a photo-radical initiator.

Examples of the radical polymerizable compound include (meth)acrylates, (meth)acrylamides, aromatic vinyls, and the like.

Examples of the (meth)acrylates that are used as the radical polymerizable compound include monofunctional (meth)acrylate, difunctional (meth)acrylate, trifunctional (meth)acrylate, tetrafunctional (meth)acrylate, pentafunctional (meth)acrylate, hexafunctional (meth)acrylate, and the like.

Examples of the monofunctional (meth)acrylate include hexyl (meth)acrylate, 2-ethylhexyl (meth)acrylate, tert-octyl (meth)acrylate, isoamyl (meth)acrylate, decyl (meth)acrylate, isodecyl (meth)acrylate, stearyl (meth)acrylate, isostearyl (meth)acrylate, cyclohexyl (meth)acrylate, 4-n-butylcyclohexyl (meth)acrylate, bornyl (meth)acrylate, isobornyl (meth)acrylate, benzyl (meth)acrylate, 2-ethylhexyl diglycol (meth)acrylate, butoxyethyl (meth)acrylate, 2-chloroethyl (meth)acrylate, 4-bromobutyl (meth)acrylate, cyanoethyl (meth)acrylate, benzyl (meth)acrylate, butoxymethyl (meth) acrylate, 3-methoxybutyl (meth)acrylate, 2-(2-butoxyethoxy)ethyl (meth)acrylate, 2-(2-methoxyethoxy)ethyl (meth)acrylate, 2,2,2-tetrafluoroethyl (meth)acrylate, 1H,1H,2H,2H-perfluorodecyl (meth)acrylate, 4-butylphenyl (meth)acrylate, phenyl (meth)acrylate, 2,4,5-tetramethylphenyl (meth)acrylate, 4-chlorophenyl (meth)acrylate, phenoxymethyl (meth)acrylate, phenoxyethyl (meth)acrylate, glycidyl (meth)acrylate, glycidyloxybutyl (meth)acrylate, glycidyloxyethyl (meth)acrylate, glycidyloxypropyl (meth)acrylate, tetrahydrofurfuryl (meth)acrylate, 2-hydroxyethyl (meth)acrylate, 3-hydroxypropyl (meth)acrylate, 2-hydroxypropyl (meth)acrylate, 2-hydroxybutyl (meth)acrylate, 4-hydroxybutyl (meth)acrylate, 3-hydroxybutyl (meth) acrylate, dimethylaminoethyl (meth)acrylate, diethylaminoethyl (meth)acrylate, dimethylaminopropyl (meth)acrylate, diethylaminopropyl (meth)acrylate, trimethoxysilylpropyl (meth)acrylate, trimethylsilylpropyl (meth)acrylate, polyethylene oxide monomethyl ether (meth)acrylate, oligoethylene oxide monomethyl ether (meth)acrylate, polyethylene oxide (meth)acrylate, oligoethylene oxide (meth)acrylate, oligoethylene oxide monoalkyl ether (meth)acrylate, polyethylene oxide monoalkyl ether (meth)acrylate, dipropylene glycol (meth)acrylate, polypropylene oxide monoalkyl ether (meth)acrylate, oligopropylene oxide monoalkyl ether (meth)acrylate, 2-methacryloyloxy ethyl succinate, 2-methacryloyloxy hexahydrophthalate, 2-methacryloyloxyethyl-2-hydroxypropyl phthalate, butoxydiethylene glycol (meth)acrylate, trifluoroethyl (meth)acrylate, perfluorooctylethyl (meth)acrylate, 2-hydroxy-3-phenoxypropyl (meth)acrylate, ethylene oxide (EO)-modified phenol (meth)acrylate, EO-modified cresol (meth)acrylate, EO-modified nonylphenol (meth)acrylate, propylene oxide (PO)-modified nanophenol (meth)acrylate, EO-modified-2-ethylhexyl (meth)acrylate, dicyclopentenyl (meth)acrylate, dicyclopentenyloxyethyl (meth) acrylate, dicyclopentanyl (meth)acrylate, (3-ethyl-3-oxetanylmethyl) (meth)acrylate, phenoxyethylene glycol (meth)acrylate, and the like.

Examples of the difunctional (meth)acrylate include 1,6-hexanediol di(meth) acrylate, 1,10-decanediol di(meth)acrylate, neopentyl glycol di(meth)acrylate, 2,4-methyl-1,5-pentanediol di(meth)acrylate, 3-methyl-1,5-pentanediol di(meth)acrylate, butylethylpropanediol di(meth)acrylate, ethoxylated cyclohexane di(meth)acrylate, polyethylene glycol di(meth)acrylate, oligoethylene glycol di(meth)acrylate, ethylene glycol di(meth)acrylate, 2-ethyl-2-butylbutanediol di(meth)acrylate, hydroxypivalic acid neopentyl glycol di(meth)acrylate, EO-modified bisphenol A di(meth) acrylate, bisphenol F polyethoxy di(meth)acrylate, polypropylene glycol di(meth)acrylate, oligopropylene glycol di(meth)acrylate, 1,4-butanediol di(meth)acrylate, 2-ethyl-2-butylpropanediol di(meth)acrylate, 1,9-nonane di(meth) acrylate, propoxylated ethoxylated bisphenol A di(meth) acrylate, tricyclodecane di(meth)acrylate, dipropylene glycol di(meth)acrylate, tripropylene glycol di(meth)acrylate, PO-modified neopentyl glycol di(meth)acrylate, and the like.

Examples of the trifunctional (meth)acrylate include trimethylolpropane tri(meth)acrylate, trimethylolethane tri(meth)acrylate, alkylene oxide-modified tri(meth)acrylate of trimethylol propane, pentaerythritol tri(meth)acrylate, dipentaerythritol tri(meth)acrylate, trimethylolpropane tri ((meth)acryloyloxypropyl) ether, isocyanuric acid alkylene oxide-modified tri(meth)acrylate, propionic acid dipentaerythritol tri(meth)acrylate, tri((meth)acryloyloxyethyl) isocyanurate, hydroxypivaldehyde-modified dimethylol propane tri(meth)acrylate, sorbitol tri(meth)acrylate, propoxylated trimethylol propane tri(meth)acrylate, ethoxylated glycerin triacrylate, and the like.

Examples of the tetrafunctional (meth)acrylate include pentaerythritol tetra(meth)acrylate, sorbitol tetra(meth)acrylate, ditrimethylolpropane tetra(meth)acrylate, propionic acid dipentaerythritol tetra(meth)acrylate, ethoxylated pentaerythritol tetra(meth)acrylate, and the like.

Examples of the pentafunctional (meth)acrylate include sorbitol penta(meth)acrylate and dipentaerythritol penta(meth)acrylate.

Examples of the hexafunctional (meth)acrylate include dipentaerythritol hexa(meth)acrylate, sorbitol hexa(meth) acrylate, alkylene oxide-modified hexa(meth)acrylate of phosphazene, ε-caprolactone-modified dipentaerythritol hexa(meth)acrylate, and the like.

Examples of the (meth)acrylamides that are used as the radical polymerizable compound include (meth)acrylamide, N-methyl(meth)acrylamide, N-ethyl(meth)acrylamide, N-propyl(meth)acrylamide, N-n-butyl(meth)acrylamide, N-t-butyl(meth)acrylamide, N-butoxymethyl(meth)acrylamide, N-isopropyl(meth)acrylamide, N-methylol(meth) acrylamide, N,N-dimethyl(meth)acrylamide, N,N-diethyl (meth)acrylamide, (meth)acryloylmorpholine, and the like.

Examples of the aromatic vinyls that are used as the radical polymerizable compound include styrene, dimethylstyrene, trimethylstyrene, isopropylstyrene, chloromethyl styrene, methoxystyrene, acetoxystyrene, chlorostyrene, dichlorostyrene, bromostyrene, methyl vinylbenzoic acid ester, 3-methylstyrene, 4-methylstyrene, 3-ethylstyrene, 4-ethylstyrene, 3-propyl styrene, 4-propyl styrene, 3-butyl styrene, 4-butyl styrene, 3-hexyl styrene, 4-hexyl styrene, 3-octyl styrene, 4-octyl styrene, 3-(2-ethylhexyl) styrene, 4-(2-ethylhexyl) styrene, allylstyrene, isopropenyl styrene, butenylstyrene, octenylstyrene, 4-t-pentoxycarbonyl styrene, 4-t-butoxystyrene, and the like.

Furthermore, examples of the radical polymerizable compound that is used in the present disclosure include vinyl esters (vinyl acetate, vinyl propionate, vinyl versatate, and the like), allyl esters (allyl acetate and the like), halogen-containing monomers (vinylidene chloride, vinyl chloride, and the like), vinyl ether (methylvinyl ether, butylvinyl ether, hexylvinyl ether, methoxyvinyl ether, 2-ethylhexylvinyl ether, methoxyethylvinyl ether, cyclohexylvinyl ether, chloroethylvinyl ether, triethylene glycol divinyl ether, and the like), vinyl cyanide ((meth)acrylonitrile and the like), olefins (ethylene, propylene, and the like), N-vinyl lactams (N-vinyl caprolactam and the like), and the like.

More specifically, it is possible to use the commercially available products described in "Crosslinking Agent Handbook" by Shinjo Yamashita (1981, Taiseisha Ltd.); "UV•EB Curing Handbook (Raw Material Edition)" by Kiyomi Kato (1985, Polymer Publication Association); "Applications and Markets of UV•EB Curing Technology" by RadTech Japan, page 79 (1989, published by CMC); "Polyester Resin Handbooks" by Eiichiro Takiyama (1988, manufactured by Nikkan Kogyo Shimbun, Ltd.), and the like and radical polymerizable or crosslinking monomers, oligomers, and polymers that are well-known in the industrial field.

One kind of the polymerizable compound may be used singly or two or more kinds of the polymerizable compounds may be jointly used. In a case in which two or more kinds of the polymerizable compounds are jointly used, a combination of (meth)acrylate and vinyl ether is preferred from the viewpoint of the curing property. In addition, in the polymerizable compound in the polymerizable composition according to the embodiment of the present disclosure, the content of a vinyl ether is preferably 1% to 40% by mass, more preferably 2% to 30% by mass, and particularly preferably 8% to 25% by mass of the total mass of (meth) acrylate.

The content of the polymerizable compound in the polymerizable composition according to the embodiment of the present disclosure is also dependent on the use thereof, but is preferably 10% to 95% by mass and more preferably 20% to 90% by mass of the total mass of the polymerizable composition from the viewpoint of the curing property.

In addition, the content ratio (mass ratio) between the photopolymerization initiator according to the embodiment of the present disclosure and the polymerizable compound in the polymerizable composition according to the embodiment of the present disclosure is preferably 1:5 to 1:1,000, more preferably 1:7 to 1:200, and still more preferably 1:10 to 1:100 (the photopolymerization initiator: the polymerizable compound).

<Colorant>

In the case of being used in an ink composition or the like, the polymerizable composition according to the embodiment of the present disclosure may include a colorant.

The colorant is not particularly limited, but is preferably a pigment or an oil-soluble dye which has excellent weather fastness and rich color reproducibility, and can be randomly selected from well-known colorants such as soluble dyes and used. As the colorant, a compound that does not function as a polymerization inhibitor is preferably selected since the compound does not degrade the sensitivity of a curing reaction by active radiation.

The pigment is not particularly limited and can be appropriately selected according to the purpose, and examples thereof include well-known organic pigments, inorganic pigments, and the like, and additionally, further include resin particles dyed by a dye and commercially available pigment dispersions or surface-treated pigments (for example, a dispersion obtained by dispersing a pigment in an insoluble resin or the like as a dispersion medium, a pigment having a surface on which a resin is grafted, and the like). Meanwhile, examples of the pigment include the pigments described in "Pigment Dictionaries" (2000) by Seishirou Itoh, W. Herbst, K. Hunger "Industrial Organic Pigments", JP2002-012607A, JP2002-188025A, JP2003-026978A, and JP2003-342503A.

Examples of the organic pigment and the inorganic pigment include a yellow pigment, a magenta pigment, a blue or cyan pigment, a green pigment, an orange pigment, a brown pigment, a violet pigment, a black pigment, a white pigment, and the like.

The yellow pigment is a pigment exhibiting a yellow color, and examples thereof include monoazo pigments such as C. I. Pigment Yellow 1 (Fast Yellow G and the like) and C. I. Pigment Yellow 74, disazo pigments such as C. I. Pigment Yellow 12 (Disazo Yellow and the like), C. I. Pigment Yellow 17, C. I. Pigment Yellow 97, C. I. Pigment Yellow 3, C. I. Pigment Yellow 16, C. I. Pigment Yellow 83, C. I. Pigment Yellow 155, and C. I. Pigment Yellow 219, non-benzidine-based azo pigments such as C. I. Pigment Yellow 180, azo lake pigments such as C. I. Pigment Yellow 100 (Tartrazine Yellow Lake and the like), condensed azo pigments such as C. I. Pigment Yellow 95 (Condensed Azo Yellow and the like), C. I. Pigment Yellow 93, C. I. Pigment Yellow 94, C. I. Pigment Yellow 128, and C. I. Pigment Yellow 166, acidic dye lake pigments such as C. I. Pigment Yellow 115 (Quinoline Yellow Lake and the like), basic dye lake pigments such as C. I. Pigment Yellow 18 (Thioflavin Lake and the like), anthraquinone pigments such as C. I. Pigment Yellow 24 (Flavanthrone Yellow and the like), quinophthalone pigments such as C. I. Pigment Yellow 110 (Quinophthalone Yellow and the like), isoindoline pigments such as C. I. Pigment Yellow 139 (Isoindoline Yellow and the like), pyrazolone pigments such as C. I. Pigment Yellow 60 (Pyrazolone Yellow and the like), acetron pigments such as C. I. Pigment Yellow 120, C. I. Pigment Yellow 154, C. I. Pigment Yellow 167, C. I. Pigment Yellow 151, C. I. Pigment Yellow 175, C. I. Pigment Yellow 180, C. I. Pigment Yellow 181, C. I. Pigment Yellow 185, and C. I. Pigment Yellow 194, metal complex salt pigments such as C. I. Pigment Yellow 150, nitroso pigments such as C. I. Pigment Yellow 153 (Nickel Nitroso Yellow and the like), metal complex salt azomethine pigments such as C. I. Pigment Yellow 117 (Copper Azomethine Yellow and the like), and the like.

The magenta pigment is a pigment exhibiting a red or magenta color, and examples thereof include monoazo-based pigments such as C. I. Pigment Red 3 (Toluidine Red and the like), B-naphthol pigments such as C. I. Pigment Red 1, C. I. Pigment Red 4, and C. I. Pigment Red 6, disazo pigments such as C. I. Pigment Red 38 (Pyrazolone Red B and the like), azo lake pigments such as C. I. Pigment Red 53:1 (Lake Red C and the like), C. I. Pigment Red 57:1

(Brilliant Carmine 6B and the like), C. I. Pigment Red 52:1, and C. I. Pigment Red 48 (B-Oxynaphthoic Acid Lake and the like), condensed azo pigments such as C. I. Pigment Red 144, C. I. Pigment Red 166, C. I. Pigment Red 220, C. I. Pigment Red 214, C. I. Pigment Red 221, C. I. Pigment Red 242 (Condensed Azo Red and the like), acidic dye lake pigments such as C. I. Pigment Red 174 (Phloxine B Lake and the like), C. I. Pigment Red 172 (Ellis Rosin Lake and the like), basic dye lake pigments such as C. I. Pigment Red 81 (Rhodamine 6G' Lake and the like), anthraquinone-based pigments such as C. I. Pigment Red 177 (Dianthraquinonyl Red and the like), thioindigo pigments such as C. I. Pigment Red 88 (Thioindigo Bordeaux and the like), perinone pigments such as C. I. Pigment Red 194 (Perinone Red and the like), perylene pigments such as C. I. Pigment Red 149, C. I. Pigment Red 179, C. I. Pigment Red 178, C. I. Pigment Red 190, C. I. Pigment Red 224, and C. I. Pigment Red 123, quinacridone pigments such as C. I. Pigment Violet 19 (unsubstituted quinacridone), C. I. Pigment Red 122, C. I. Pigment Red 262, C. I. Pigment Red 207, and C. I. Pigment Red 209, isoindolinone pigments such as C. I. Pigment Red 180 (Isoindolinone Red 2BLT and the like), alizarin lake pigments such as C. I. Pigment Red 83 (Madder Lake and the like), naphtholone pigments such as C. I. Pigment Red 171, C. I. Pigment Red 175, C. I. Pigment Red 176, C. I. Pigment Red 185, and C. I. Pigment Red 208, naphthol AS-based pigments such as C. I. Pigment Red 247, naphthol AS pigments such as C. I. Pigment Red 2, C. I. Pigment Red 5, C. I. Pigment Red 21, C. I. Pigment Red 170, C. I. Pigment Red 187, C. I. Pigment Red 256, C. I. Pigment Red 268, and C. I. Pigment Red 269, diketo-pyrrolo-pyrrole pigments such as C. I. Pigment Red 254, C. I. Pigment Red 255, C. I. Pigment Red 264, and C. I. Pigment Red 272, and the like.

The cyan pigment is a pigment exhibiting a blue or cyan color, and examples thereof include disazo-based pigments such as C. I. Pigment Blue 25 (Dianisidine Blue and the like), phthalocyanine pigments such as C. I. Pigment Blue 15, C. I. Pigment Blue 15:1, C. I. Pigment Blue 15:2, C. I. Pigment Blue 15:3, C. I. Pigment Blue 15:4, C. I. Pigment Blue 15:6, and C. I. Pigment Blue 16 (Phthalocyanine Blue and the like), acidic dye lake pigments such as C. I. Pigment Blue 24 (Peacock Blue Lake and the like), basic dye lake pigments such as C. I. Pigment Blue 1 (Victoria Pure Blue BO Lake and the like), anthraquinone-based pigments such as C. I. Pigment Blue 60 (Indanthrone Blue and the like), alkali blue pigments such as C. I. Pigment Blue 18 (Alkali Blue V-5:1), and the like.

The green pigment is a pigment exhibiting a green color, and examples thereof include phthalocyanine pigments such as C. I. Pigment Green 7 (Phthalocyanine Green) and C. I. Pigment Green 36 (Phthalocyanine Green), azo metal complex pigments such as C. I. Pigment Green 8 and C. I. Pigment Green 10, and the like.

The orange pigment is a pigment exhibiting an orange color, and examples thereof include isoindoline-based pigments such as C. I. Pigment Orange 66 (Isoindoline Orange), anthraquinone-based pigments such as C. I. Pigment Orange 51 (Dichloropyranthrone Orange), B-naphtol pigments such as C. I. Pigment Orange 2, C. I. Pigment Orange 3, and C. I. pigment Orange 5, naphthol AS pigments such as C. I. Pigment Orange 4, C. I. Pigment Orange 22, C. I. Pigment Orange 24, C. I. Pigment Orange 38, and C. I. Pigment Orange 74, isoindolinone pigments such as C. I. Pigment Orange 61, perinone pigments such as C. I. Pigment Orange 43, disazo pigments such as C. I. Pigment Orange 15 and C. I. Pigment Orange 16, quinacridone pigments such as C. I. Pigment Orange 48 and C. I. Pigment Orange 49, acetolone pigments such as C. I. Pigment Orange 36, C. I. Pigment Orange 62, C. I. Pigment Orange 60, C. I. Pigment Orange 64, and C. I. Pigment Orange 72, pyrazolone pigments such as C. I. Pigment Orange 13 and C. I. Pigment Orange 34, and the like.

The brown pigment is a pigment exhibiting a brown color, and examples thereof include naphtholone pigments such as C. I. Pigment Brown 25 and C. I. Pigment Brown 32 and the like.

The violet pigment is a pigment exhibiting a violet color, and examples thereof include naphtholone pigments such as C. I. Pigment Violet 32, perylene pigments such as C. I. Pigment Violet 29, naphthol AS pigments such as C. I. Pigment Violet 13, C. I. Pigment Violet 17, and C. I. Pigment Violet 50, dioxazine pigment such as C. I. Pigment Violet 23 and C. I. Pigment Violet 37, and the like.

The black pigment is a pigment exhibiting a black color, and examples thereof include carbon black such as MOGUL E, titanium black, indazine pigments such as C. I. Pigment Black 1 (Aniline Black), perylene pigments such as C. I. Pigment Black 31 and C. I. Pigment Black 32, and the like.

Examples of the white pigment include basic lead carbonate ($2PbCO_3Pb(OH)_2$, so-called silver white), zinc oxide (ZnO, so-called zinc white), titanium oxide ($TiO_2$, so-called titanium white), strontium titanate ($SrTiO_3$, so-called titanium strontium white), and the like. Inorganic particles that are used in the white pigment may be a single body or may be, for example, an oxide of silicon, aluminum, zirconium, titanium, or the like, an organic metal compound, or composite particles with an organic compound.

Among these, the titanium oxide is preferably used since the titanium oxide has a smaller specific weight and a larger refractive index than other white pigments and is also chemically and physically stable and thus have a great covering power and a great coloring force as a pigment and, furthermore, has excellent durability with respect to acids, alkalis, and other environments. Meanwhile, other white pigments (which may be white pigments other than the white pigments described above) may be jointly used with the titanium oxide.

For the dispersion of the pigment, it is possible to preferably use a dispersion apparatus, for example, a ball mill, a sand mill, an attritor, a roll mill, a jet mill, a homogenizer, a paint shaker, a kneader, an agitator, a Henschel mixer, a colloid mill, an ultrasound homogenizer, a pearl mill, or a wet-type jet mill.

In the present disclosure, during the dispersion of the pigment, a dispersant described below is particularly preferably added.

In addition, during the dispersion of the pigment, as a dispersion aid, a synergist suitable for a variety of pigments may be added as necessary. The content of the dispersion aid in the ink composition is preferably 1 to 50 parts by mass with respect to 100 parts by mass of the pigment.

The dispersion medium that is used during the dispersion of the pigment in the polymerizable composition is not particularly limited and can be appropriately selected depending on the purpose, and, for example, the polymerizable compound having a low molecular weight may be used as the dispersion medium or the solvent may be used as the dispersion medium. However, the polymerizable composition according to the embodiment of the present disclosure is a radiation-curable polymerizable composition, and, for example, since the polymerizable composition is cured after being applied onto a recording medium, solvents are preferably not contained. This is because, in a case in which a solvent remains in a cured substance, the solvent resistance deteriorates, and a problem of a volatile organic compound (VOC) of the remaining solvent is caused. Therefore, it is preferable to use the polymerizable compound as the dispersion medium and select, particularly, a polymerizable compound having the lowest viscosity from the viewpoint of improving dispersion suitability or the handleability of the polymerizable composition.

The average particle diameter of the pigment is not particularly limited, and can be appropriately selected depending on the purpose, but is preferably approximately 0.01 µm to 0.4 µm and more preferably 0.02 µm to 0.2 µm since the color developability becomes superior as the particles become finer. In addition, the maximum particle diameter of the pigment is preferably 3 µm or less and more preferably 1 µm or less. The particle diameter of the pigment can be adjusted by means of the selection of the pigment, the dispersant, and a dispersion medium, the setting of dispersion conditions and filtration conditions, and the like, and it is possible to suppress the clogging of head nozzles and maintain the preservation stability of ink, the ink transparency, and the curing sensitivity by controlling the particle diameter of the pigments.

Meanwhile, the particle diameter of the pigment can be measured using a well-known measurement method. Specifically, the particle diameter can be measured using a centrifugal sedimentation light transmission method, an X-ray transmission method, a laser diffraction and scattering method, or a dynamic light scattering method.

One kind of the colorant may be used singly or two or more kinds of the colorants may be jointly used.

The content of the colorant in the polymerizable composition is appropriately selected depending on color and intended uses and is preferably 0.01% to 30% by mass of the mass of the entire polymerizable composition.

<Additional Polymerization Initiators>

The polymerizable composition according to the embodiment of the present disclosure may further contain an additional polymerization initiator other than the photopolymerization initiator according to the embodiment of the present disclosure as necessary, but preferably does not contain any additional polymerization initiator.

Examples of the additional polymerization initiator include photopolymerization initiators other than the photopolymerization initiator according to the embodiment of the present disclosure and thermopolymerization initiators, polymerization initiators for radical polymerization or cation polymerization are preferred, and radical polymerization initiators are particularly preferred. It is possible to use, for example, the polymerization initiator described in JP2009-138172A.

One kind of the additional polymerization initiator may be used singly or two or more kinds of the additional polymerization initiators may be jointly used.

The total content of the additional polymerization initiators is preferably 10% by mass or less, more preferably 5% by mass or less, still more preferably 1% by mass or less, and particularly preferably 0% by mass of the entire polymerizable composition. In the above-described range, the curing property is excellent.

In addition, the total content of the additional polymerization initiator is preferably smaller than the content of the photopolymerization initiator according to the embodiment of the present disclosure.

<Dispersant>

The polymerizable composition according to the embodiment of the present disclosure may further contain a dispersant. Particularly, in a case in which the pigment is used, the polymerizable composition preferably contains a dispersant in order to stably disperse the pigment in the ink composition. The dispersant is preferably a polymer dispersant. Meanwhile, the "polymer dispersant" in the present disclosure refers to a dispersant having a weight-average molecular weight of 1,000 or more.

Examples of the polymer dispersant include DISPERBYK-101, DISPERBYK-102, DISPERBYK-103, DISPERBYK-106, DISPERBYK-111, DISPERBYK-161, DISPERBYK-162, DISPERBYK-163, DISPERBYK-164, DISPERBYK-166, DISPERBYK-167, DISPERBYK-168, DISPERBYK-170, DISPERBYK-171, DISPERBYK-174, and DISPERBYK-182 (manufactured by BYK Chemie); EFKA4010, EFKA4046, EFKA4080, EFKA5010, EFKA5207, EFKA5244, EFKA6745, EFKA6750, EFKA7414, EFKA745, EFKA7462, EFKA7500, EFKA7570, EFKA7575, EFKA7580, and EFKA7701 (manufactured by Efka Additives); DISPERSE AID 6, DISPERSE AID 8, DISPERSE AID 15, and DISPERSE AID 9100 (manufactured by San Nopco Limited); a variety of SOLSPERSE dispersants (manufactured by Noveon) such as SOLSPERSE 3000, 5000, 9000, 12000, 13240, 13940, 17000, 22000, 24000, 26000, 28000, 32000, 36000, 39000, 41000, and 71000; ADEKA PLURONIC L31, F38, L42, L44, L61, L64, F68, L72, P95, F77, P84, F87, P94, L101, P103, F108, L121, and P-123 (manufactured by ADEKA Corporation), IONET S-20 (manufactured by Sanyo Chemical Industries, Ltd.), DISPALON KS-860, 873 SN, 874 (polymer dispersants), #2150 (aliphatic polyhydric carboxylic acid), and #7004 (polyether ester-type dispersant) (manufactured by Kusumoto Chemicals, Ltd.).

The content of the dispersant in the polymerizable composition is appropriately selected depending on intended uses and is preferably 0.05% to 15% by mass of the mass of the entire polymerizable composition.

<Surfactant>

The polymerizable composition according to the embodiment of the present disclosure may further contain a surfactant.

Examples of the surfactant include the surfactants described in JP1987-173463A (JP-S62-173463A) and JP1987-183457A (JP-S62-183457A). Examples thereof include anionic surfactants such as dialkyl sulfosuccinates, alkylnaphthalene sulfonates, and fatty acid salts, nonionic surfactants such as polyoxyethylene alkyl ethers, polyoxyethylene alkyl allyl ethers, acetylene glycols, polyoxyethylene•polyoxypropylene block copolymers, and cationic surfactants such as alkyl amine salts and quaternary ammonium salts. In addition, as the surfactant, fluorine-based surfactants (for example, an organic fluoro compound and the like) or silicone-based surfactants (for example, a polysiloxane compound and the like) may be used. The organic fluoro compound is preferably hydrophobic. Examples of the organic fluoro compound include fluorine-based surfactants, oil-form fluorine-based compounds (for example, fluorine oil), and solid-like fluorine compound resins (for example, tetrafluoro ethylene resins) and include the compounds described in JP1982-009053B (JP-S57-009053B) (Sections 8 to 17) and JP1987-135826A (JP-S62-135826A). The polysiloxane compound is preferably a modified polysiloxane compound in which an organic group is introduced into some of methyl groups in dimethyl polysiloxane. Examples of modification include polyether modification, methyl styrene modification, alcohol modification, alkyl modification, aralkyl modification, fatty acid ester modification, epoxy modification, amine modification, amino modification, mercapto modification, and the like, but the modification is not particularly limited thereto. These modification methods may be used in combination. In addition, among these, a polyether-modified polysiloxane compound is preferred from the viewpoint of the improvement of jetting stability in an ink jet. Examples of the polyether-modified polysiloxane compound include SILWET L-7604, SILWET L-7607N, SILWET FZ-2104, and SILWET FZ-2161 (manufactured by Nippon Unika Co., Ltd.), BYK306, BYK307, BYK331, BYK333, BYK347, and BYK348 (manufactured by BYK Chemie), KF-351A, KF-352A, KF-353, KF-354L, KF-355A, KF-615A, KF-945, KF-640, KF-642, KF-643, KF-6020, X-22-6191, X-22-4515, KF-6011, KF-6012, KF-6015, and KF-6017 (manufactured by Shin-Etsu Chemical Co., Ltd.).

Among these, silicone-based surfactants are preferred.

The content of the surfactant in the polymerizable composition according to the embodiment of the present disclosure is appropriately selected depending on intended uses and is preferably 0.0001% to 1% by mass of the mass of the entire polymerizable composition.

<Solvent>

The polymerizable composition according to the embodiment of the present disclosure may further contain a solvent.

Examples of the solvent include ketone-based solvents such as acetone, methyl ethyl ketone, and diethyl ketone, alcohol-based solvents such as methanol, ethanol, 2-propanol, 1-propanol, 1-butanol, and tert-butanol, chlorine-based solvents such as chloroform and methylene chloride, aromatic solvents such as benzene and toluene, ester-based solvents such as ethyl acetate, butyl acetate, and isopropyl acetate, ether-based solvents such as diethyl ether, tetrahydrofuran, and dioxane, glycol ether-based solvents such as ethylene glycol monomethyl ether, ethylene glycol dimethyl ether, and tripropylene glycol monomethyl ether, cyclic ester-based solvents such as γ-butyrolactone, amide-based solvents such as 2-methyl pyrrolidone and 2-pyrrolidone, and the like.

In this case, the addition of the solvent that does not cause any problem with the solvent resistance or VOC is effective, and the amount of the solvent is preferably 0.1% to 5% by mass and more preferably 0.1% to 3% by mass of the total mass of the polymerizable composition.

To the polymerizable composition, a solvent may be added as a dispersion medium for a variety of components such as the pigment, or the polymerizable compound may be used as a dispersion medium without adding any solvents, but the polymerizable composition preferably does not contain any solvents.

<Sensitizer>

The polymerizable composition according to the embodiment of the present disclosure may further contain a sensitizer.

Examples of the sensitizer include polynuclear aromatic compounds (for example, pyrene, perylene, triphenylene, 2-ethyl-9,10-dimethoxyanthracene, and the like), xanthenes (for example, fluorescein, eosin, erythrosin, rhodamine B, rose bengal, and the like), cyanines (for example, thiacarbocyanine, oxacarbocyanine, and the like), merocyanines (for example, merocyanine, carbomerocyanine, and the like), thiazines (for example, thionine, methylene blue, toluidine blue, and the like), acridines (for example, acridine orange, chloroflavin, acriflavine, and the like), anthraquinones (for example, anthraquinone and the like), squaryliums (for example, squalium and the like), coumarins (for example, 7-diethylamino-4-methylcoumarin and the like), thioxanthones (for example, isopropylthioxanthone and the like), thiochromanones (for example, thiochromanone and the like), and the like. Among these, thioxanthones are preferred as the sensitizer. Examples of the thioxanthones include diethylthioxanthone (DETX), isopropylthioxanthone (ITX), SP 7010 (manufactured by Lambson Limited), and the like. Additionally, the sensitizers described in WO2013/146062A also can be used.

<Additional Additives>

The polymerizable composition according to the embodiment of the present disclosure may further contain additional additives depending on a variety of uses.

As the additional additives, a variety of well-known additives can be used.

As the additional additives, it is possible to add, for example, an alkali-soluble resin, a co-sensitizer, an ultraviolet absorbent, a basic compound, a leveling additive, a matting agent, a wax, a polymerization inhibitor, an antioxidant, a viscosity imparting agent, and the like.

In a case in which the polymerizable composition according to the embodiment of the present disclosure is used as the ink jet ink composition, in consideration of the jettability from an ink jet nozzle of the polymerizable composition, the viscosity of the polymerizable composition at the temperature during jetting is preferably 0.5 to 30 mPa·s, more preferably 0.5 to 20 mPa·s, and most preferably 1 to 15 mPa·s. The compositional ratio is preferably adjusted and determined so as to obtain a viscosity in the above-described range.

Meanwhile, the viscosity of the polymerizable composition at 25° C. (room temperature) is preferably 1 mPa·s or more and 200 mPa·s or less, more preferably 2 mPa·s or more and 50 mPa·s or less, and still more preferably 2.5 mPa·s or more and 30 mPa·s or less. In a case in which the viscosity at room temperature is set to be high, even in the case of using a porous recording medium, the permeation of the polymerizable composition into the recording medium is prevented, it becomes possible to reduce non-cured monomers, furthermore, it is possible to suppress the bleeding of dots during the landing of ink liquid droplets, and consequently, image quality improves. In addition, in a case in which the viscosity of the polymerizable composition at 25° C. is 200 mPa·s or less, the delivery of the ink composition to an ink jet head or the like in a device is easy.

Meanwhile, as the viscosity of the composition of the present disclosure, a value measured using VISCOMETER TV-22 (manufactured by Toki Sangyo Co., Ltd.) under the above-described temperature condition is used.

In a case in which the polymerizable composition according to the embodiment of the present disclosure is used as the ink jet ink composition, the surface tension of the polymerizable composition is preferably 20 to 40 mN/m and more preferably 23 to 35 mN/m. In a case in which recording is carried out on a variety of recording media such as a polyolefin, PET, coated paper, and uncoated paper, the surface tension is preferably 20 mN/m or more from the viewpoint of bleeding and permeation and preferably 40 mN/m or less from the viewpoint of wettability.

Meanwhile, as the surface tension of the composition of the present disclosure, a value measured using Automatic Surface Tensiometer CBVP-Z (manufactured by Kyowa Interface Science Co., Ltd.) under a condition of a liquid temperature of 25° C.

(Ink Jet Recording Method)

The polymerizable composition according to the embodiment of the present disclosure can be preferably used as the ink jet ink composition.

An ink jet recording method according to the embodiment of the present disclosure is not particularly limited, but preferably includes a step of jetting the polymerizable composition according to the embodiment of the present disclosure onto a recording medium (a support, a recording material, or the like) using an ink jet method and a step of curing the polymerizable composition by irradiating the jetted polymerizable composition with active radiation. The ink jet recording method according to the embodiment of the present disclosure includes the above-described two steps, thereby forming an image on a recording medium using the cured polymerizable composition.

In addition, a printed article of the present disclosure is a printed article recorded using the polymerizable composition according to the embodiment of the present disclosure and preferably a printed article recorded using the ink jet recording method according to the embodiment of the present disclosure.

In the ink jet recording method according to the embodiment of the present disclosure, it is possible to use an ink jet recording device described below in detail.

<Ink Jet Recording Device>

The ink jet recording device that can be used in the ink jet recording method according to the embodiment of the present disclosure is not particularly limited, and a well-known ink jet recording device capable of achieving a target resolution can be randomly selected and used. That is, any well-known ink jet recording devices including commercially available products can be used to jet the polymerizable composition to a recording medium in the ink jet recording method according to the embodiment of the present disclosure.

Examples of the ink jet recording device that can be used in the present disclosure include devices including an ink supply system, a temperature sensor, and an active energy ray source.

The ink supply system is made up of, for example, a base tank including the polymerizable composition according to the embodiment of the present disclosure, a supply pipe, an ink supply tank immediately ahead of an ink jet head, a filter, and a piezo-type ink jet head. The piezo-type ink jet head can be driven so as to be capable of jetting multi-sized dots of preferably 1 to 100 pl and more preferably 8 to 30 pl at a resolution of preferably 320×320 to 4,000×4,000 dpi, more preferably 400×400 to 1,600×1,600 dpi, and still more preferably 720×720 dpi. Meanwhile, "dots per inch (dpi)" mentioned in the present disclosure refers to the number of dots per 2.54 cm.

As described above, the polymerizable composition according to the embodiment of the present disclosure, the polymerizable composition to be jetted is preferably maintained at a constant temperature, and thus the ink jet recording device preferably comprises means for stabilizing the polymerizable composition temperature. Portions in which the temperature is maintained constant are all of pipe systems and members from an ink tank (an intermediate tank in a case in which there is the intermediate tank) to a nozzle injection surface. That is, heat insulation and heating can be carried out in a portion from the ink supply tank to the ink jet head.

The temperature control method is not particularly limited, but it is preferable to, for example, provide a plurality of temperature sensors in the respective pipe portions and control heating depending on the flow rate of the polymerizable composition and the environmental temperature. The temperature sensors can be provided in the ink supply tank and the vicinity of a nozzle of the ink jet head. In addition, a head unit that heats the polymerizable composition is preferably thermally shielded or insulated so as to prevent the device main body from being affected by the external temperature. In order to shorten the printing initiation time necessary for heating or reduce the loss of heat energy, it is preferable to thermally insulate a heating unit from other portions and decrease the heat capacity of the entire heating unit.

In addition, the temperature of the polymerizable composition during jetting is preferably maintained constant as much as possible. It is appropriate to set the control width of the temperature of the polymerizable composition during jetting to preferably the set temperature±5° C., more preferably the set temperature±2° C., and still more preferably the set temperature±1° C.

Next, irradiation with active radiation will be described.

The polymerizable composition jetted onto the recording medium cures by irradiation with active radiation. This is because the polymerization initiator that is included in the polymerizable composition according to the embodiment of the present disclosure degrades by irradiation with active radiation and generates a polymerization initiating species such as a radical, and a polymerization reaction of the polymerizable compound is initiated and accelerated due to the function of the initiating species. At this time, in a case in which a sensitizer is present together with the polymerization initiator in the polymerizable composition, the sensitizer in the system absorbs active radiation, thus moves into an excited state, and comes into contact with the polymerization initiator so as to accelerate the degradation of the polymerization initiator, whereby it is possible to achieve a curing reaction with a higher sensitivity.

Here, as the active radiation being used, it is possible to use an α ray, a γ ray, an electron beam, an X-ray, an ultraviolet ray, a visible ray, an infrared ray, or the like. The peak wavelength of the active radiation is also dependent on the absorption characteristics of the sensitizer, and is, for example, preferably 200 to 600 nm, more preferably 300 to 450 nm, and still more preferably 320 to 420 nm. The active energy ray is particularly preferably an ultraviolet ray having a peak wavelength in a range of 340 to 400 nm.

In addition, the polymerization initiation system of the polymerizable composition according to the embodiment of the present disclosure is a low-power active energy ray having a sufficient sensitivity. Therefore, it is appropriate to cure the polymerizable composition at an exposed surface illuminance of preferably 10 to 4,000 mW/cm$^2$ and more preferably 20 to 2,500 mW/cm$^2$.

As an active radiation source, a mercury lamp, a gas laser, a solid-state laser, or the like is mainly used, and, as a light source that is used to cure an ultraviolet ray-photocurable ink jet ink composition, a mercury lamp and a metal halide lamp are widely known. However, from the viewpoint of the current environmental protection, the removal of mercury is strongly desired, and the replacement into a GaN-based semiconductor ultraviolet light emitting device is extremely useful in an industrial and environmental sense. Furthermore, an LED (UV-LED) and an LD (UV-LD) are small-sized, long-service life, high-efficiency, and low-cost light sources and are expected as a photocurable ink jet light source.

In addition, a light emitting diode (LED) and a laser diode (LD) can be used as the active radiation source. Particularly, in a case in which an ultraviolet ray source is required, a violet LED and an ultraviolet LD can be used. For example, Nichia Corporation launches a violet LED in which the main emission spectrum has a wavelength between 365 nm and 420 nm. Furthermore, in a case in which a shorter wavelength is required, the specification of U.S. Pat. No. 6,084,250A discloses an LED capable of emitting active radiation having a center between 300 nm and 370 nm. In addition, other ultraviolet LEDs can be procured, and irradiation with radiation having a different ultraviolet band is possible. In the present disclosure, a particularly preferred active energy ray source is a UV-LED and a UV-LED having a peak wavelength particularly preferably at 340 to 400 nm.

Meanwhile, the maximum illuminance of the LED on the recording medium is preferably 10 to 2,000 mW/cm$^2$, more preferably 20 to 1,000 mW/cm$^2$, and particularly preferably 50 to 800 mW/cm$^2$.

The polymerizable composition according to the embodiment of the present disclosure is appropriately irradiated with the above-described active radiation for preferably 0.01 to 120 seconds and more preferably 0.1 to 90 seconds.

The irradiation conditions and the basic irradiation method of the active radiation are disclosed by JP1985-132767A (JP-S60-132767A). Specifically, light sources are provided on both sides of a head unit including a jetting device of the polymerizable composition, and the head unit and the light sources are scanned in a so-called shuttle manner, thereby carrying out the irradiation. The irradiation with the active radiation is carried out for a certain time (preferably 0.01 to 0.5 seconds, more preferably 0.01 to 0.3 seconds, and still more preferably 0.01 to 0.15 seconds) after the landing of the ink composition. In a case in which the time taken from the landing of the ink composition to the irradiation is controlled to be extremely short as described above, it becomes possible to prevent the polymerizable composition landed on the recording medium from bleeding before being cured. In addition, it is possible to expose the polymerizable composition before the polymerizable composition permeates into a deep portion of a porous recording medium which the light source does not reach, and thus the remaining of unreacted monomers can be suppressed, which is preferable.

Furthermore, the curing may be completed using a different light source that does not accompany driving. WO99/054415A discloses a method in which an optical fiber is used as an irradiation method or a method in which a recording portion is irradiated with UV light by striking a collimated light source to a mirror surface provided on a side surface of the head unit, and these curing methods can also be applied to the ink jet recording method according to the embodiment of the present disclosure.

The polymerizable composition according to the embodiment of the present disclosure is preferably used in a form of an ink set made up of a plurality of ink jet ink compositions.

In the ink jet recording method according to the embodiment of the present disclosure, the order of individual ink compositions to be jetted is not particularly limited, but it is preferable to impart a coloring ink composition having a high brightness to the recording medium, and, in a case in which yellow, cyan, magenta, and black are used, it is preferable to impart yellow, cyan, magenta, and black in this order onto the recording medium. In addition, in a case in which white is added to the above-described colors and used, it is preferable to impart white, yellow, cyan, magenta, and black in this order onto the recording medium. Furthermore, the present disclosure is not limited thereto, it is also possible to preferably use an ink set which includes ink compositions of at least seven colors of yellow, light cyan, light magenta, cyan, magenta, black, and white, and, in this case, it is preferable to impart white, light cyan, light magenta, yellow, cyan, magenta, and black in this order onto the recording medium.

<Recording Medium>

The recording medium to which the polymerizable composition according to the embodiment of the present disclosure can be applied is not particularly limited, and it is possible to use paper such as ordinary uncoated paper and coated paper, a variety of nonabsorbent resin materials that are used for so-called soft packaging, and resin films obtained by forming the above-described resin materials in a film shape.

Examples of a variety of plastic films include polyethylene terephthalate (PET) films, biaxially oriented polystyrene (OPS) films, biaxially oriented polypropylene (OPP) films, biaxially oriented nylon (ONy) films, polyvinyl chloride (PVC) films, polyethylene (PE) films, cellulose triacetate (TAC) films, and the like.

Additionally, examples of plastic that can be used as the recording medium material include polycarbonate, acrylic resins, acrylonitrile-butadiene-styrene (ABS) copolymers, polyacetal, polyvinyl alcohol (PVA), rubber, and the like. In addition, metals or glass are also used as the recording medium.

The polymerizable composition according to the embodiment of the present disclosure contains the polymerization initiator according to the embodiment of the present disclosure and thus can be preferably used as a curable ink jet ink composition that can be cured by irradiation with the active radiation. In addition, the curable composition according to the present disclosure is also capable of directly forming high-quality images on a nonabsorbent recording medium on the basis of digital data and is thus preferably used for the production of printed articles having a large area.

The polymerizable composition of the embodiment of the present disclosure contains the polymerization initiator of the embodiment of the present disclosure and thus can be cured with a low exposure amount. Therefore, it is considered that the use of an inexpensive light source having a low exposure intensity reduces systems or running costs and the shortening of the exposure time contributes to an improvement of the printing rate. Furthermore, the fast curing rate after exposure enables the suppression of the bleeding of images, and clear images can be formed.

(Acylphosphine Oxide Compound)

An acylphosphine oxide compound according to the embodiment of the present disclosure is represented by Formula 1-1 or Formula 2-1.

Formula 1-1

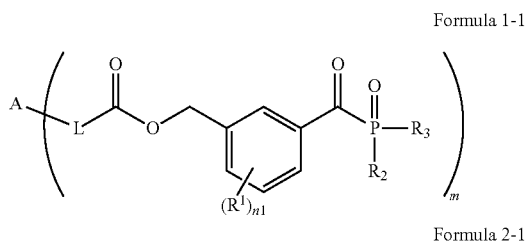

Formula 2-1

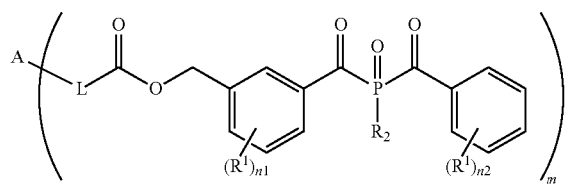

In Formula 1-1 and Formula 2-1, A represents an m-valent group, L's each independently represent a single bond or a divalent linking group, $R^1$'s each independently represent an alkyl group having 1 to 8 carbon atoms, an aryl group having 6 to 20 carbon atoms, or an alkoxy group having 1 to 4 carbon atoms, $R^2$ and $R^3$ each independently represent an alkyl group, an aryl group, or an alkoxy group, m represents an integer of 3 or more, n1's each independently represent an integer of 0 to 4, and n2's each independently represent an integer of 0 to 5.

The acylphosphine oxide compound according to the embodiment of the present disclosure is preferably represented by Formula 1-2 or Formula 2-2.

Formula 1-2

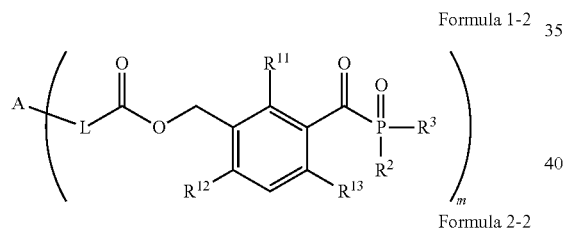

Formula 2-2

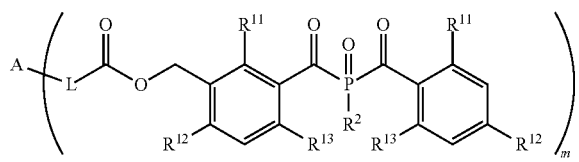

In Formula 1-2 and Formula 2-2, A represents an m-valent group, L's each independently represent a single bond or a divalent linking group, $R^2$ and $R^3$ each independently represent an alkyl group, an aryl group, or an alkoxy group, $R^{11}$ to $R^{13}$ each independently represent an alkyl group having 1 to 8 carbon atoms, an aryl group having 6 to 20 carbon atoms, or an alkoxy group having 1 to 4 carbon atoms, and m represents an integer of 3 or more.

Preferred aspects of the acylphosphine oxide compound according to the embodiment of the present disclosure are the same as the preferred aspects of the specific acylphosphine oxide compound described above as the photopolymerization initiator according to the embodiment of the present disclosure respectively.

The acylphosphine oxide compound according to the embodiment of the present disclosure can be preferably used as a photopolymerization initiator.

The producing method of the acylphosphine oxide compound according to the embodiment of the present disclosure is not particularly limited, the acylphosphine oxide compound may be produced using a well-known producing method, and the above-described producing method of the specific acylphosphine oxide compound is preferably exemplified.

EXAMPLES

Hereinafter, an embodiment of the present invention will be described in detail using examples, but the present disclosure is not limited to these examples. Meanwhile, unless particularly otherwise described, "parts" and "%" are mass-based.

In addition, Exemplary Compounds 1 to 7 used in the examples are respectively A-1 to A-7 described above, and Exemplary Compound 8 is A-16 described above.

[Synthesis of Exemplary Compound 1]

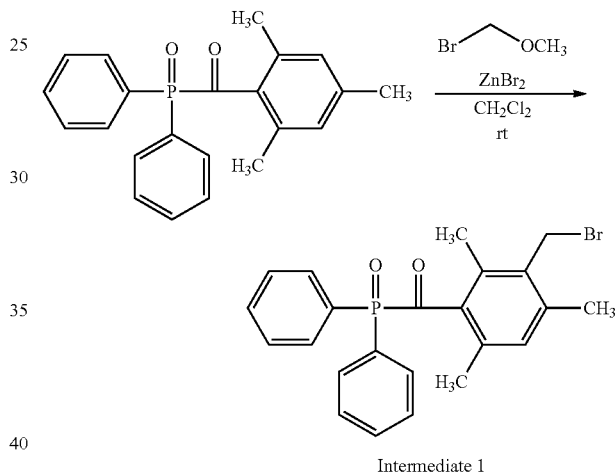

Intermediate 1

<Synthesis of Intermediate 1>

Dichloromethane ($CH_2Cl_2$) (133 parts by mass) was added to and dissolved in TPO (100 parts by mass, 287 molar equivalent, LUCIRIN (registered trademark) TPO manufactured by BASF Japan Ltd.), and then zinc (II) bromide ($ZnBr_2$, 194 parts by mass, 432 molar equivalent) was added thereto in a split manner and stirred so as to be dissolved. After that, bromomethyl methyl ether (43.05 parts by mass, 344 molar equivalent) was added dropwise thereto and stirred at room temperature (rt, 10° C. to 35° C. which will be true in the following description) for 10 hours. A reaction liquid was slowly added dropwise to ice water so as to stop the reaction, then, extracted using dichloromethane, washed with water, and dried using magnesium sulfate. Next, the resultant was filtered, and the filtrate was condensed and then purified using a silica gel column (hexane/ethyl acetate=40/60 (volume ratio)). A solid obtained by dispersing the filtrate using hexane was filtered and washed with hexane, thereby obtaining a white intermediate 1 (110 parts by mass, 87%).

$^1$H NMR (CDCl$_3$, 400 MHz) δ: 1.93 (3H, s), 2.09 (3H, s), 2.38 (3H, s), 4.46 (2H, s), 6.85 (1H, s), 7.48-7.61 (6H, m), 7.97-8.01 (4H, m).

<Synthesis of Exemplary Compound 1 (A-1)>
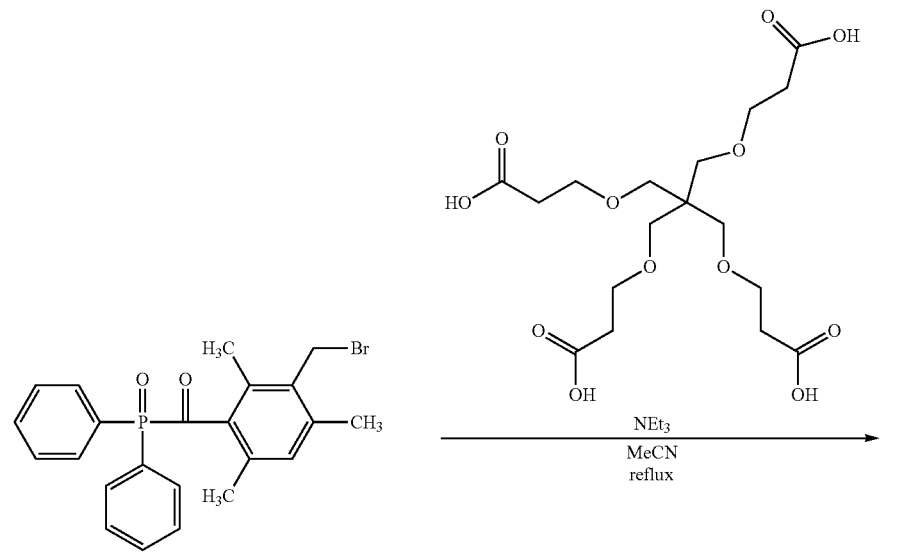
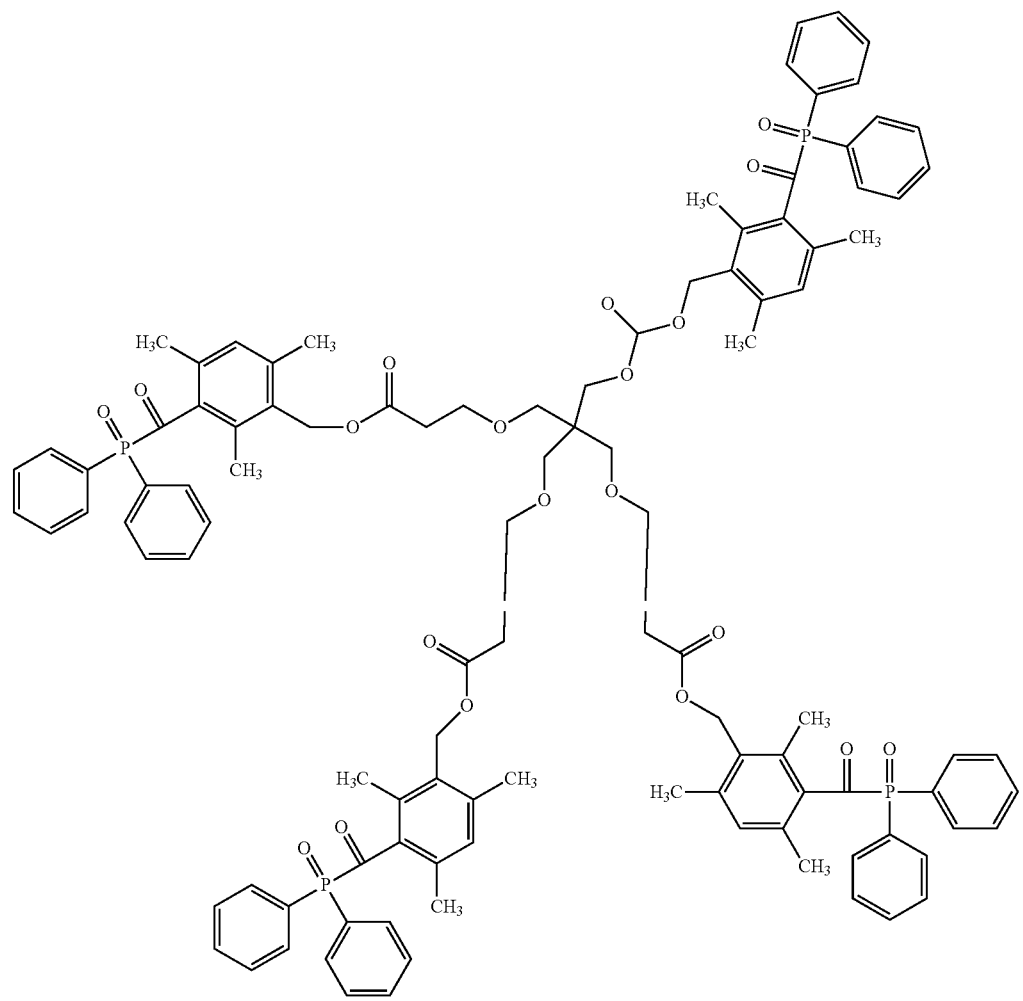
Exemplary Compound 1

Acetonitrile (MeCN) (23.6 parts by mass) was added to TETRAACID (the tetravalent carboxylic acid compound, manufactured by Frontier Scientific, Inc., 1.92 parts by mass, 4.53 molar equivalent), the intermediate 1 (10.0 parts by mass, 22.7 molar equivalent), and triethylamine ($NEt_3$, 4.59 parts by mass, 45.3 molar equivalent) and refluxed and stirred for five hours. A reaction liquid was condensed, ethyl acetate (89.7 parts by mass) was added thereto, dispersed therein, and filtered, then, a filtrate was purified using a silica gel column (ethyl acetate), thereby obtaining a white Exemplary Compound 1 (5.75 parts by mass, 68%).

$^1$H NMR ($CDCl_3$, 400 MHz) δ: 1.94 (12H, s), 2.05 (12H, s), 2.30 (12H, s), 2.46 (8H, J=8.0 Hz, t), 3.21 (8H, s), 3.52 (8H, J=8.0 Hz, t), 5.09 (8H, s), 6.85 (4H, m), 7.48-7.59 (24H, m), 7.97-8.02 (16H, m).

[Syntheses of Exemplary Compound 2 to Exemplary Compound 5 (A-2 to A-5)]

Exemplary Compound 2 to Exemplary Compound 5 were synthesized in the same manner as Exemplary Compound 1 except for the fact that hemimellitic acid, trimesic acid, 1,3,5-benzene triacetic acid, or 2,3,6,7,10,11-triphenylene hexacarboxylic acid were used instead of TETRAACID, and the intermediate 1 (1.25 molar equivalent) was added to the carboxylic acid group (1 molar equivalent).

[Synthesis of Exemplary Compound 6 (A-6)]

Exemplary Compound 6 was synthesized in the same manner as Exemplary Compound 1 except for the fact that IRGACURE (registered trademark) 819 (manufactured by BASF Japan Ltd.) was used instead of TPO.

[Synthesis of Exemplary Compound 7 (A-7)]

Exemplary Compound 7 was synthesized in the same manner as Exemplary Compound 1 except for the fact that glycol ether diamine tetraacetic acid was used instead of TETRAACID.

$^1$H NMR ($CDCl_3$, 400 MHz) δ: 1.94 (12H, s), 2.02 (12H, s), 2.30 (12H, s), 2.87 (4H, J=6.0 Hz, t), 3.42 (4H, s), 3.51 (4H, J=6.0 Hz, t), 3.53 (8H, s), 5.11 (8H, s), 6.85 (4H, m), 7.48-7.59 (24H, m), 7.97-8.02 (16H, m).

[Synthesis of Exemplary Compound 8 (A-16)]

Exemplary Compound 8 was synthesized in the same manner as Exemplary Compound 1 except for the fact that 2-[(carboxymethyl)thio]butanedioic acid was used instead of TETRAACID.

[Syntheses of Comparative Compound 1 to Comparative Compound 3]

Comparative Compound 1 was synthesized with reference to JP2014-185319A, and Comparative Compounds 2 and 3 were synthesized with reference to WO2013/091521A respectively.

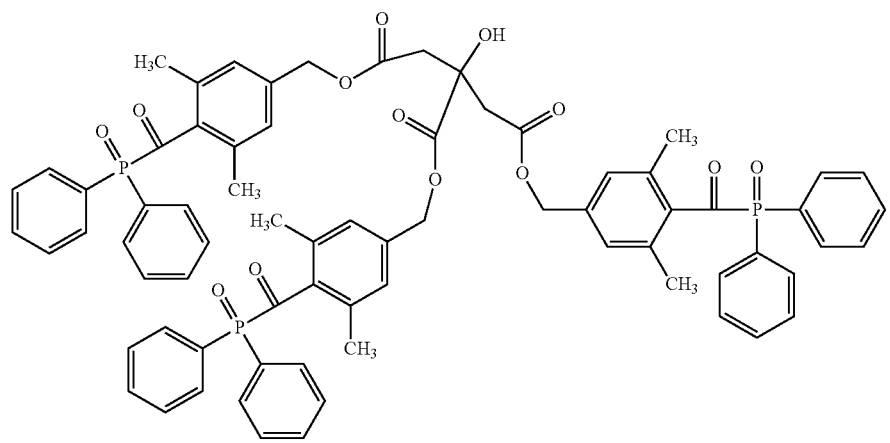

Comparative Compound 1

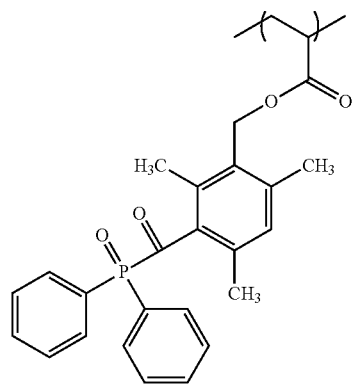

Comparative Compound 2

Mw = 2,000

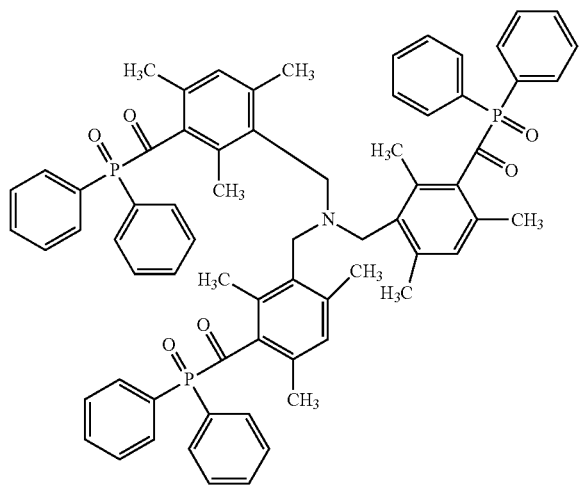

Comparative Compound 3

Example 1 to Example 7 and Comparative
Example 1 to Comparative Example 3

—Production Method of Ink Composition (Polymerizable Composition)—

3-Methyl-1,5-pentanediol diacrylate (SR341, manufactured by Sartomer) (80 parts by mass) as a polymerizable compound, a compound shown in Table 1 (8 parts by mass) as a photopolymerization initiator, SP7010 (manufactured by Lambson Limited) (2 parts by mass) as a sensitizer, a cyan millbase A (10 parts by mass), and a surfactant (BYK307 silicone-based surfactant, manufactured by BYK Chemie) (0.1 parts by mass) were added, mixed, and stirred together, thereby obtaining each ink composition.

In addition, the cyan millbase A was prepared as described below.

—Preparation of Cyan MillBase A—

Heliogen Blue D 7110 F (a cyan pigment, manufactured by BASF Japan Ltd.) (300 parts by mass), SR9003 (PO-modified neopentyl glycol diacrylate, manufactured by Sartomer) (620 parts by mass), and SOLSPERSE (registered trademark) 32000 (a dispersant manufactured by Noveon International) (80 parts by mass) were stirred and mixed together, thereby obtaining a cyan millbase A. Meanwhile, the cyan millbase A was prepared by putting the above-described components into a disperser motor mill M50 (manufactured by Eiger) and carrying out dispersion using zirconia beads having a diameter of 0.65 mm at a circumferential speed of 9 m/s for four hours.

—Ink Jet Image Recording—

Recording was carried out on a recording medium using an ink jet recording device having a piezo-type ink jet nozzle and the ink composition obtained above. An ink supply system was made up of a base tank, a supply pipe, an ink supply tank immediately ahead of an ink jet head, a filter, and a piezo-type ink jet head (the diameter of an opening portion of the nozzle was 25 μm). In addition, in the ink supply system, heat insulation and heating can be carried out in a portion from the ink supply tank to the ink jet head. Temperature sensors were provided in the ink supply tank and the vicinity of the nozzle of the ink jet head, and the temperature was controlled so as to be 40° C.±2° C. at all times in the nozzle portion. The piezo-type ink jet head was driven so that 1 to 10 picoliters (pl) of multi-sized dots could be injected at a resolution of 4,800×4,800 dpi. After the landing, UV light was focused to an exposed surface illuminance of 700 mW/cm$^2$, and the exposure system, the main scanning rate, and the injection frequency were adjusted so that irradiation began 0.1 seconds after the landing of the ink composition on the recording medium. In addition, the exposure time was set to be variable, and exposure energy was radiated. As an ultraviolet lamp, a HAN250NL high-cure mercury lamp (manufactured by GS Yuasa Corporation) was used. Meanwhile, dpi mentioned in the present disclosure refers to the number of dots per 2.54 cm. As the recording medium, an ester film E5000 (film thickness: 125 μm, manufactured by Toyobo Co., Ltd.) was used.

<Evaluation of Elution (Migration) Amount>

A solid image having an average film thickness of 6 μm obtained by the above-described ink jet image recording using the obtained ink composition was cut into a size of one square decimeter, a liquid mixture (10 ml) of water and ethanol (mass ratio=20:80) was added dropwise onto a printed surface, and a printed article was put into a glass airtight container and left to stand at 40° C. for 10 days in order to prevent the volatilization of the liquid mixture. After that, the total amount of the elution amounts of the photopolymerization initiator (acylphosphine oxide compound) and a degraded substance of the photopolymerization initiator from the printed article included in the liquid mixture was determined by high-performance liquid chromatography (HPLC) and evaluated using the following five levels.

A: Less than 10 ppb
B: 10 ppb or more and less than 30 ppb
C: 30 ppb or more and less than 100 ppb
D: 100 ppb or more and less than 300 ppb
E: 300 ppb or more <Evaluation of Curing Sensitivity>

A solid image having an average film thickness of 6 μm was drawn according to the above-described ink jet recording method and was irradiated with ultraviolet rays. The amount of exposure energy (mJ/cm$^2$) at which the pressure sensitive adhesive feeling disappeared on the ultraviolet-irradiated image surface was defined as the curing sensitivity. A small numerical value indicates a high sensitivity.

In addition, the curing sensitivity was evaluated using the following standards.

A+: Less than 500 mJ/cm$^2$
A: 500 mJ/cm$^2$ or more and less than 1,000 mJ/cm$^2$
B: 1,000 mJ/cm$^2$ or more and less than 1,500 mJ/cm$^2$
C: 1,500 mJ/cm$^2$ or more and less than 2,000 mJ/cm$^2$
D: 2,000 mJ/cm$^2$ or more and less than 2,500 mJ/cm$^2$
E: 2,500 mJ/cm$^2$ or more <Ink Jet Jettability (Jettability)>

The obtained ink composition was jetted from 256 nozzles using a piezo-type ink jet head QS-256/30 (manufactured by FUJIFILM DIMA TIX) at an amount of jetted liquid droplets being each 30 pL, a frequency of 33 kHz, and 25° C. for 10 minutes, and nozzle clogging after the jetting was evaluated. Evaluation was carried out using the following five levels.

A: There is no clogging.
B: The number of clogged nozzles is 1 or 2.
C: The number of clogged nozzles is 3 to 5.
D: The number of clogged nozzles is 6 to 20.
E: The number of clogged nozzles is 21 or more.

<Preservation Stability of Ink Composition>

After the obtained ink composition was stored at room temperature (25° C.) for three months and then filtered using a 0.4 μm filter, the ratio of the photopolymerization initiator in the ink composition was computed in terms of percent by area of HPLC and evaluated as described below.

A: The amount of the percent by area of HPLC of the photopolymerization initiator changed for three months of the storage from the production of the ink composition was less than 2%.

B: The amount of the percent by area of HPLC of the photopolymerization initiator changed for three months of the storage from the production of the ink composition was 2% or more and less than 5%.

C: The amount of the percent by area of HPLC of the photopolymerization initiator changed for three months of the storage from the production of the ink composition was 5% or more and less than 7%.

D: The amount of the percent by area of HPLC of the photopolymerization initiator changed for three months of the storage from the production of the ink composition was 7% or more and less than 10%.

E: The amount of the percent by area of HPLC of the photopolymerization initiator changed for three months of the storage from the production of the ink composition was 10% or more.

Examples 8 and 9

Ink compositions were prepared respectively in the same manner as in Example 1 except for the fact that 3-methyl- 1,5-pentanediol diacrylate and triethylene glycol divinyl ether were added as the polymerizable compound as much as the following parts by mass and the respective evaluations were carried out.

Example 8: 65 Parts by mass of 3-methyl-1,5-pentanediol diacrylate and 15 parts by mass of triethylene glycol divinyl ether Example 9: 75 Parts by mass of 3-methyl-1,5-pentanediol diacrylate and 5 parts by mass of triethylene glycol divinyl ether Example 10

An ink composition was prepared respectively in the same manner as in Example 1 except for the fact that Exemplary Compound 8 was used as the photopolymerization initiator and the respective evaluations were carried out.

The evaluation results of the examples and the comparative examples are summarized in Table 1.

TABLE 1

|  | Compound | Evaluation results | | | |
| --- | --- | --- | --- | --- | --- |
|  |  | Migration amount | Curing sensitivity | Jettability | Preservation stability |
| Example 1 | Exemplary Compound 1 | A | B | A | A |
| Example 2 | Exemplary Compound 2 | B | B | A | A |
| Example 3 | Exemplary Compound 3 | A | B | A | A |
| Example 4 | Exemplary Compound 4 | A | B | A | A |
| Example 5 | Exemplary Compound 5 | A | B | B | B |
| Example 6 | Exemplary Compound 6 | B | A | A | A |
| Example 7 | Exemplary Compound 7 | B | B | A | B |
| Example 8 | Exemplary Compound 1 | A | A+ | A | A |
| Example 9 | Exemplary Compound 1 | A | A | A | A |
| Example 10 | Exemplary Compound 8 | B | B | A | B |
| Comparative Example 1 | Comparative Compound 1 | B | C | B | A |
| Comparative Example 2 | Comparative Compound 2 | A | C | D | D |
| Comparative Example 3 | Comparative Compound 3 | C | B | A | D |

As is clear from the results of Table 1, it is found that, in the case of using the photopolymerization initiator according to the embodiment of the present disclosure, the migration amount is small, and the curing sensitivity and the ink jet jettability are excellent.

In addition, in the case of using the photopolymerization initiator according to the embodiment of the present disclosure, the preservation stability as an ink composition is also excellent.

In addition, in the case of using the acylphosphine compound having a $C_n$ symmetry such as $C_3$ symmetry or $C_4$ symmetry as described in Example 1 to Example 4, the migration amount becomes smaller.

In the case of using the acylphosphine compound having the m being an integer of 3 or more and 5 or less as described in Example 1 to Example 5, the jettability and the preservation stability are superior.

As described in Example 1 and Example 6, in a case in which the photopolymerization initiator is an acylphosphine compound represented by Formula 1-1, the migration amount becomes smaller, and, in a case in which the photopolymerization initiator is an acylphosphine compound represented by Formula 2-1, the curing sensitivity is superior.

In a case in which A is an m-valent group not having any of an amino bond, a thioether bond, and a halogen atom, and L is a divalent linking group not having any of an amino bond, a thioether bond, and a halogen atom or a single bond as described in Example 1, Example 7, and Example 10, the migration amount is smaller, and the preservation stability is superior.

In the case of jointly using 3-methyl-1,5-pentanediol diacrylate and triethylene glycol divinyl ether as the polymerizable compound as described in Example 1, Example 8, and Example 9, the curing sensitivity is superior.

The disclosure of JP2016-174987 filed on Sep. 7, 2016 is incorporated into the present specification by reference.

All of the documents, the patent applications, and the technical standards described in the present specification are incorporated into the present specification by reference to the same extent as each of the documents, the patent applications, and the technical standards is specifically and individually described in the present specification.

What is claimed is:

1. A photopolymerization initiator which is an acylphosphine oxide compound represented by Formula 1-1 or Formula 2-1,

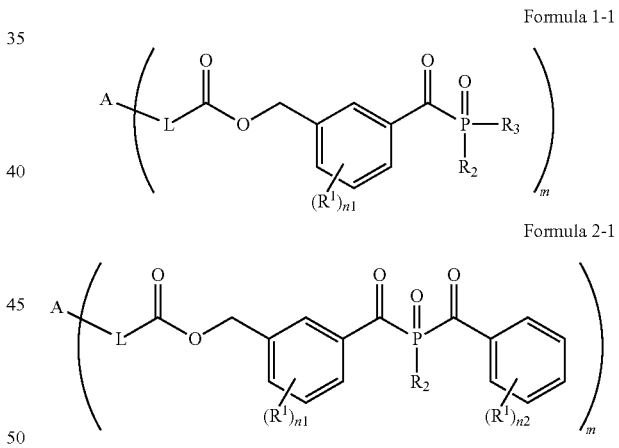

wherein, in Formula 1-1 and Formula 2-1, A represents an m-valent group, L's each independently represent a single bond or a divalent linking group, $R^1$'s each independently represent an alkyl group having 1 to 8 carbon atoms, an aryl group having 6 to 20 carbon atoms, or an alkoxy group having 1 to 4 carbon atoms, $R^2$ and $R^3$ each independently represent an alkyl group, an aryl group, or an alkoxy group, m represents an integer of 3 or more, n1's each independently represent an integer of 0 to 4, and n2's each independently represent an integer of 0 to 5.

2. The photopolymerization initiator according to claim 1, wherein A is an m-valent group obtained by bonding two or more structures selected from the group consisting of a carbon atom, an m-valent hydrocarbon group having 1 to 30 carbon atoms, a mono- or higher-valent hydrocarbon group having 1 to 30 carbon atoms, an oxygen atom, a nitrogen atom, and a sulfur atom.

3. The photopolymerization initiator according to claim 1, wherein A is an m-valent group having a ring structure, an m-valent hydrocarbon group having 1 to 3 carbon atoms, or a carbon atom.

4. The photopolymerization initiator according to claim 1, wherein A is an m-valent group not having any of an amino bond, a thioether bond, and a halogen atom, and L is a divalent linking group not having any of an amino bond, a thioether bond, and a halogen atom or a single bond.

5. The photopolymerization initiator according to claim 1 which is an acylphosphine oxide compound represented by Formula 1-2 or Formula 2-2, Formula 1-2

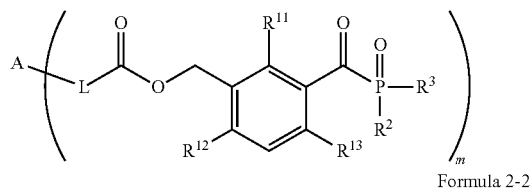

Formula 2-2

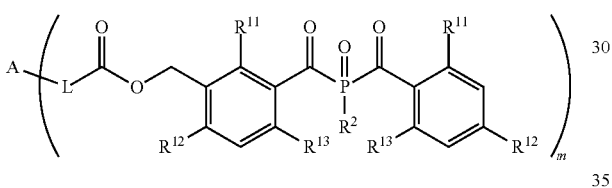

wherein, in Formula 1-2 and Formula 2-2, A represents an m-valent group, L's each independently represent a single bond or a divalent linking group, $R^2$ and $R^3$ each independently represent an alkyl group, an aryl group, or an alkoxy group, $R^{11}$ to $R^{13}$ each independently represent an alkyl group having 1 to 8 carbon atoms, an aryl group having 6 to 20 carbon atoms, or an alkoxy group having 1 to 4 carbon atoms, and m represents an integer of 3 or more.

6. The photopolymerization initiator according to claim 1, wherein m is an integer of 3 to 5.

7. The photopolymerization initiator according to claim 1, wherein the acylphosphine oxide compound is a compound having a $C_n$ symmetry; here, n represents an integer of 3 to 24.

8. A polymerizable composition comprising:
the photopolymerization initiator according to claim 1; and
a polymerizable compound.

9. An ink jet recording method comprising:
a step of jetting the polymerizable composition according to claim 8 onto a recording medium using an ink jet method; and
a step of curing the polymerizable composition by irradiating the jetted polymerizable composition with active radiation.

10. An acylphosphine oxide compound represented by Formula 1-1 or Formula 2-1,

Formula 1-1

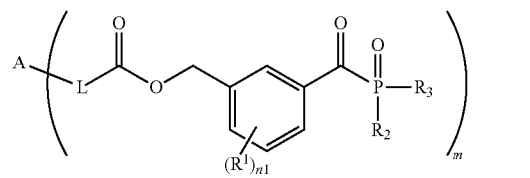

Formula 2-1

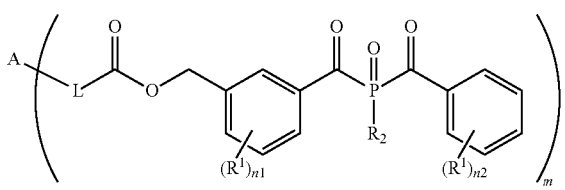

wherein, in Formula 1-1 and Formula 2-1, A represents an m-valent group, L's each independently represent a single bond or a divalent linking group, $R^1$'s each independently represent an alkyl group having 1 to 8 carbon atoms, an aryl group having 6 to 20 carbon atoms, or an alkoxy group having 1 to 4 carbon atoms, $R^2$ and $R^3$ each independently represent an alkyl group, an aryl group, or an alkoxy group, m represents an integer of 3 or more, n1's each independently represent an integer of 0 to 4, and n2's each independently represent an integer of 0 to 5.

11. The acylphosphine oxide compound according to claim 10, wherein A is an m-valent group having a ring structure, an m-valent hydrocarbon group having 1 to 3 carbon atoms, or a carbon atom.

12. The acylphosphine oxide compound according to claim 10, wherein A is an m-valent group not having any of an amino bond, a thioether bond, and a halogen atom, and L is a divalent linking group not having any of an amino bond, a thioether bond, and a halogen atom or a single bond.

13. The acylphosphine oxide compound according to claim 10 represented by Formula 1-2 or Formula 2-2, Formula 1-2

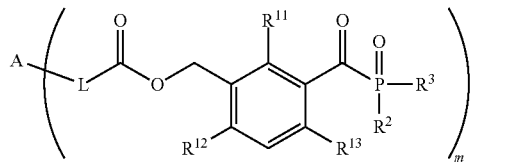

Formula 2-2

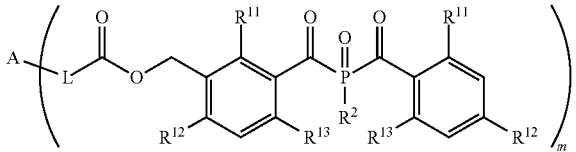

wherein, in Formula 1-2 and Formula 2-2, A represents an m-valent group, L's each independently represent a single bond or a divalent linking group, $R^2$ and $R^3$ each independently represent an alkyl group, an aryl group, or an alkoxy group, $R^{11}$ to $R^{13}$ each independently represent an alkyl group having 1 to 8 carbon atoms, an aryl group having 6 to 20 carbon atoms, or an alkoxy group having 1 to 4 carbon atoms, and m represents an integer of 3 or more.

14. The acylphosphine oxide compound according to claim 10, wherein m is an integer of 3 to 5.

15. The acylphosphine oxide compound according to claim 10 having a $C_n$ symmetry, wherein n represents an integer of 3 to 24.

\* \* \* \* \*